(12) United States Patent
Partin et al.

(10) Patent No.: US 7,691,133 B2
(45) Date of Patent: Apr. 6, 2010

(54) SYSTEMS AND METHODS FOR BONE FIXATION

(75) Inventors: Jason Ian Partin, Encinitas, CA (US); Robert J. Ball, San Marcos, CA (US); Ian A. Trail, Manchester (GB)

(73) Assignee: Integra Lifesciences Corporation, Plainsboro, NJ (US)

( * ) Notice: Subject to any disclaimer, the term of this patent is extended or adjusted under 35 U.S.C. 154(b) by 961 days.

(21) Appl. No.: 11/292,333

(22) Filed: Nov. 30, 2005

(65) Prior Publication Data

US 2006/0264936 A1 Nov. 23, 2006

Related U.S. Application Data

(60) Provisional application No. 60/631,951, filed on Nov. 30, 2004.

(51) Int. Cl.
*A61B 17/80* (2006.01)

(52) U.S. Cl. .................................................... 606/289

(58) Field of Classification Search ......... 606/300–306, 606/313, 314, 319, 280, 281, 286, 287, 288, 606/289, 290, 295, 297
See application file for complete search history.

(56) References Cited

U.S. PATENT DOCUMENTS

| | | | |
|---|---|---|---|
| 4,056,020 A * | 11/1977 | Coviello | ................... 81/177.2 |
| 4,858,602 A | 8/1989 | Seidel et al. | |
| 5,336,225 A | 8/1994 | Zang | |
| 5,403,136 A | 4/1995 | Mathys | |
| 5,501,695 A | 3/1996 | Anspach, Jr. et al. | |
| 5,681,311 A | 10/1997 | Foley et al. | |
| 5,683,390 A * | 11/1997 | Metz-Stavenhagen et al. | .......................... 606/278 |
| 5,713,904 A | 2/1998 | Errico et al. | |
| 5,741,259 A | 4/1998 | Chan | |
| 5,807,396 A | 9/1998 | Raveh | |
| 5,891,145 A | 4/1999 | Morrison et al. | |
| 5,902,303 A | 5/1999 | Eckhof et al. | |

(Continued)

OTHER PUBLICATIONS

Official Action-Final dated Aug. 18, 2009 received in U.S. Appl. No. 11/010,825.

*Primary Examiner*—Anu Ramana
(74) *Attorney, Agent, or Firm*—Jenkins, Wilson, Taylor & Hunt, P.A.

(57) ABSTRACT

Systems and methods for bone fixation are disclosed. A fixation system can have a planar fixation device and a laterally-fixed fixation apparatus. The planar fixation device can have a planar surface and at least one opening having side walls defining an at least generally cylindrical shape. The laterally-fixed fixation apparatus can have an at least generally cylindrical shaped head portion having outer wall sections at least partially surrounding a central hollow area. The head portion can have an inner bottom surface. An expander hub is provided in the fixation apparatus for positioning at least partially within the central hollow area of the head portion and can be seated at least partially on the inner bottom surface of the head portion. The expander hub is rotatable to force the outer wall sections of the head portion outwardly for engaging and locking the fixation apparatus in place in the opening. The fixation apparatus is further adapted for rotation about a longitudinal axis of the fixation apparatus without lateral toggle movement relative to the planar surface of the planar fixation device. In other aspects, systems for fixating an orthopedic guide and systems and methods for compressing bone portions are also provided.

44 Claims, 26 Drawing Sheets

U.S. PATENT DOCUMENTS

| | | |
|---|---|---|
| 5,911,721 A | 6/1999 | Nicholson et al. |
| 5,954,722 A | 9/1999 | Bono |
| 5,968,044 A | 10/1999 | Nicholson et al. |
| 6,019,759 A | 2/2000 | Rogozinski |
| 6,022,352 A | 2/2000 | Vandewalle |
| 6,083,227 A | 7/2000 | Saurat et al. |
| 6,235,033 B1 * | 5/2001 | Brace et al. .................. 606/288 |
| 6,258,089 B1 | 7/2001 | Campbell et al. |
| 6,355,044 B1 | 3/2002 | Hair |
| 6,440,135 B2 | 8/2002 | Orbay et al. |
| 6,579,290 B1 * | 6/2003 | Hardcastle et al. .......... 606/247 |
| 6,595,993 B2 | 7/2003 | Donno et al. |
| 6,599,290 B2 | 7/2003 | Bailey et al. |
| 6,605,090 B1 | 8/2003 | Trieu et al. |
| 6,656,181 B2 | 12/2003 | Dixon et al. |
| 6,663,635 B2 | 12/2003 | Frigg et al. |
| 6,689,135 B2 | 2/2004 | Enayati |
| 6,733,502 B2 | 5/2004 | Altarac et al. |
| 6,770,073 B2 | 8/2004 | McDevitt et al. |
| 7,063,701 B2 * | 6/2006 | Michelson .................. 606/307 |
| 7,104,991 B2 | 9/2006 | Dixon et al. |
| 7,137,987 B2 | 11/2006 | Patterson et al. |

* cited by examiner

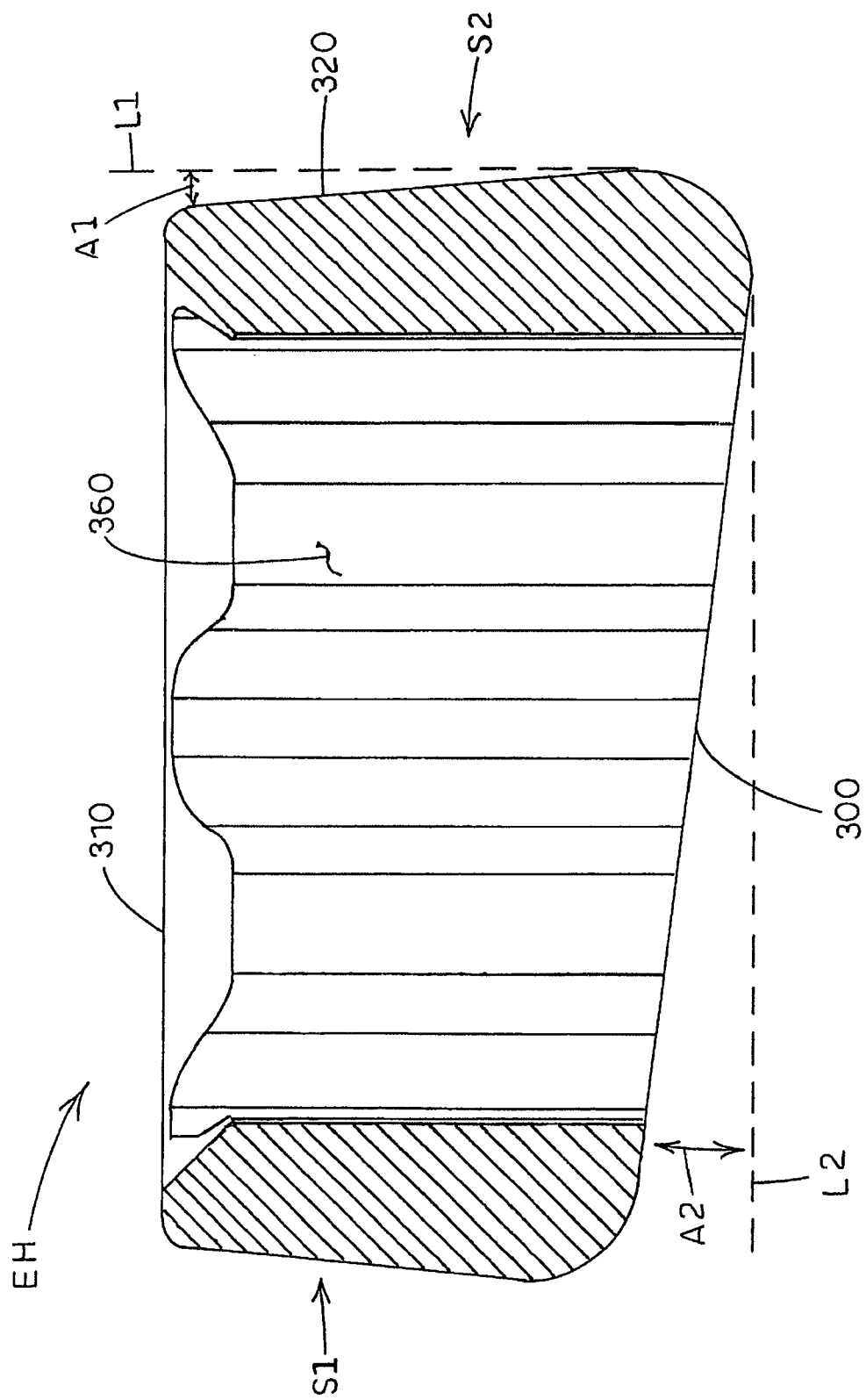

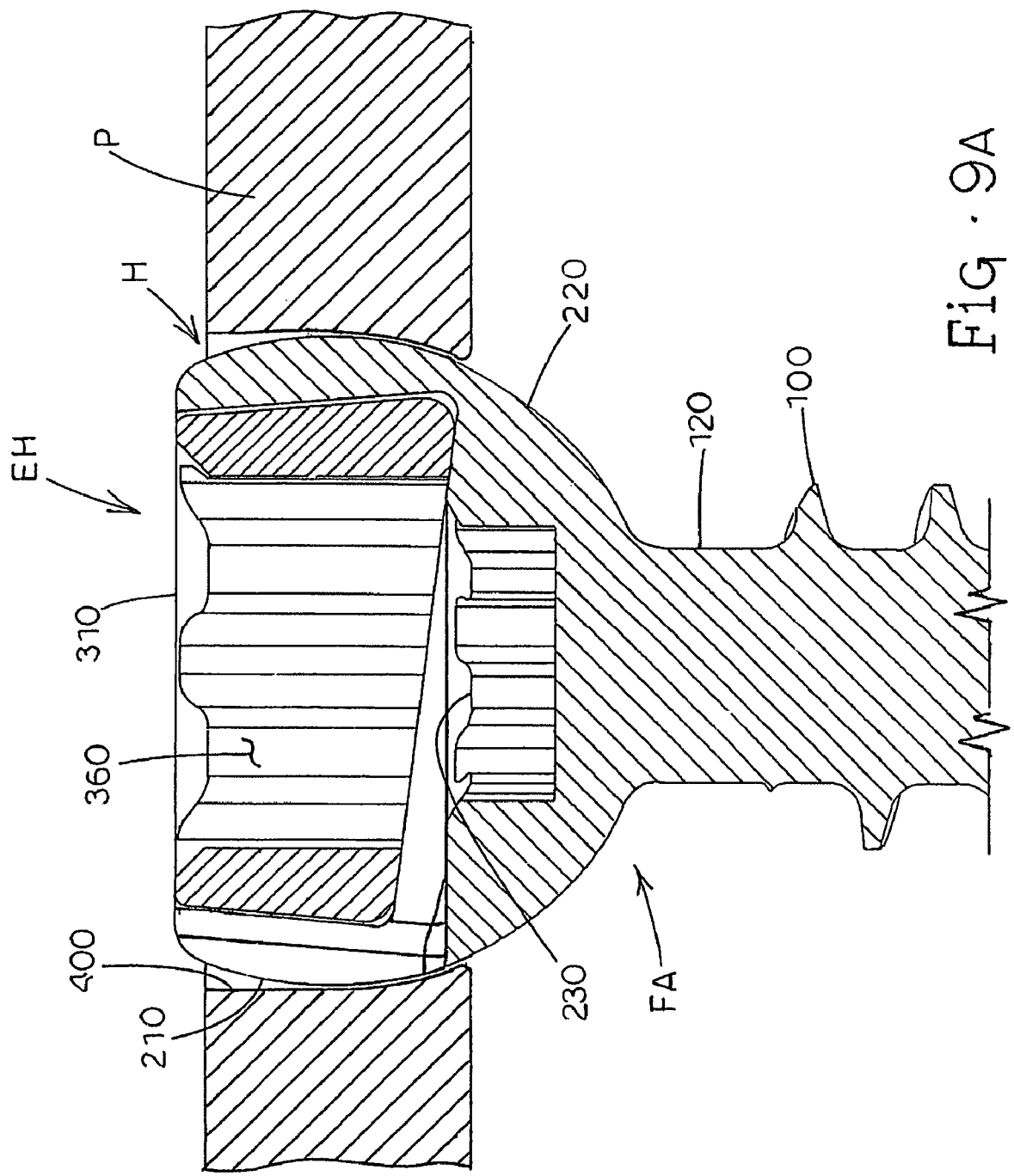

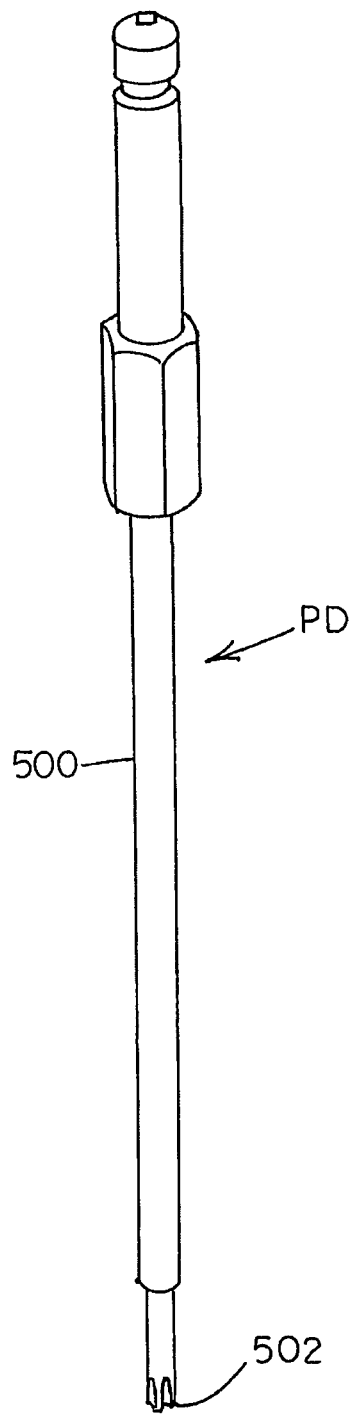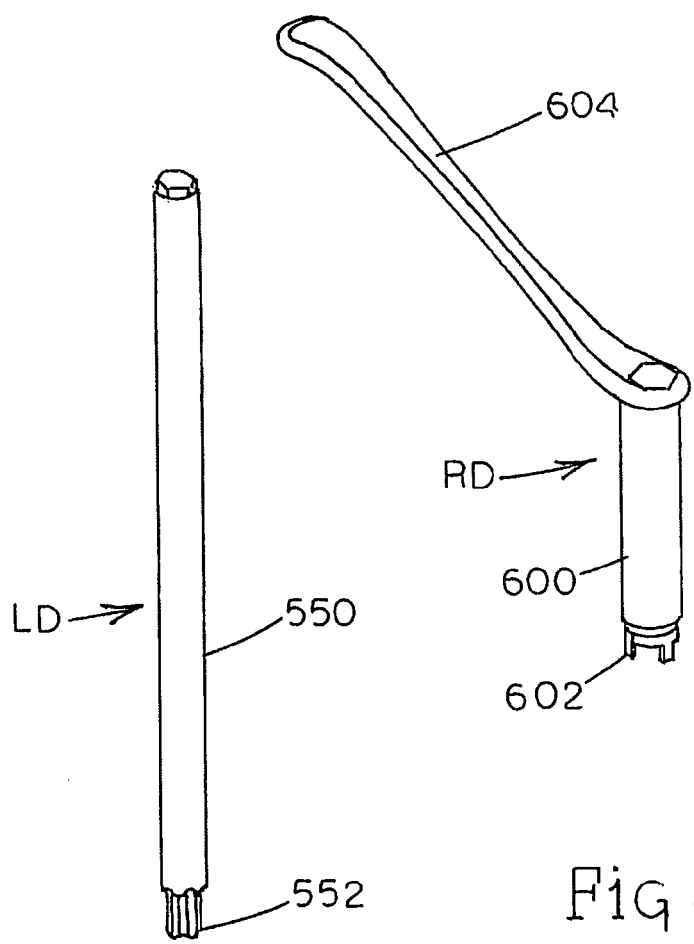
Fig. 11A  Fig. 11B  Fig. 11C

SYSTEMS AND METHODS FOR BONE FIXATION

RELATED APPLICATIONS

This application claims the benefit of U.S. Provisional Patent Application Ser. No. 60/631,951, filed Nov. 30, 2004 and U.S. patent application Ser. No. 11/010,825, filed Dec. 13, 2004, the disclosures of which are incorporated herein by reference.

TECHNICAL FIELD

The present subject matter relates generally to bone fixation and, more particularly to systems for bone fixation utilizing a plate and fixation apparatus system to lock in variable or fixed locked positions in order to fixate bone; systems for fixating an orthopedic guide; and systems and methods for compressing bone portions.

BACKGROUND ART

A variety of apparatuses and methods are known in the field of orthopedics for reducing, fixing and generally assisting the healing of fractured bones. In some cases, these apparatuses and methods require surgical intervention. Open reduction internal fixation (ORIF) is a developed art with respect to some portions of the body; however, many complications can exist which can prevent successful or optimal outcomes in all cases utilizing ORIF. Treatment methods can also significantly impact healing time, pain and functional outcomes. Moreover, the necessity of reducing operative time is driven both by patient risk of infection, and aesthetic complications, and health care costs. Thus, efforts continue to be made to improve fixation devices and surgical techniques in an attempt to improve surgical outcomes, costs and operative times.

Several factors are considered to be well known which can have significant impact in predicting outcomes of ORIF. These factors include:
1. Prominence of hardware, leading to soft tissue abrasion and general inflammation.
2. Accurate reduction of fracture site providing proper alignment in all degrees of freedom.
3. Reliable fixation that rigidly approximates bone segments during healing.
4. Production of adequate and predictable compression across fracture sites which provides impetus for improved healing.
5. Minimization of skin incision and exposure to patient.
6. Reduced operative times.

Thus, it is desirable to utilize a fracture fixation apparatus and method which provides for low-profile hardware, or hardware countersunk into bone, which reduces or eliminates soft tissue abrasions and inflammation. Additionally, it is desirable to utilize an apparatus and method that provides for reproducible reduction, fixation, and also accurate bone compression to optimize the healing process. Such an apparatus and method must also minimize skin incision and provide a method that is simple and timely in terms of operating room resources and patient risk. Since fractures can occur in all bones of the body, both large and small, it is further desirable to utilize a consistent apparatus and method that can be used and scaled to fit all size applications regardless of the size of a bone fracture.

Fixation plates are common apparatuses used in orthopedic surgery for fixing two or more bone fragments together. Commonly, a plate with several holes defined in the plate is placed adjacent to bone fragments, and screws are driven through the plate holes and into the bone fragments. This method can often provide a satisfactory reduction and fixation where sufficient bony material is available for firmly grasping and orienting a screw/plate construct. More specifically, when a fixation apparatus is able to penetrate and engage two bone cortices, the fixation apparatus is firmly supported in two locations and will thus be rotationally aligned with the plate. If the fixation apparatus is, however, only able to grasp one cortice, and in a normal case, the proximal cortice, rotational alignment is not firmly engaged between the fixation apparatus and the plate and accurate reduction of the fixation site may not be maintained. This problem is also common in the areas of the body not involving particularly long bones, such as the hand, foot and spine. This problem also commonly exists in unhealthy (rheumatoid or osteoporotic) bone that simply cannot purchase bone as firmly as healthy bone.

A variety of apparatuses and methods have existed and exist in the prior art relating to bone fracture repair. The first generation of designs for screw/plate hardware used in fracture repair consisted of simply designed mechanisms using conventional hardware and materials compatible with the application. There was little effort to reduce the profile to protect soft tissue or control the position. The second generation added to the technology of the first generation by simply making allowance for the screw to sit into the profile of the plate (countersunk) so that soft tissue abrasion was minimized.

The third generation utilized a spherical countersunk screw in plate design as it became evident as plates were used more widely through the body that it was desirable to allow the screw to be positioned in many or a range or angles relative to the plate. By creating a sphere and globular socket mechanism, a solid construct could be obtained with the screw at any angle to the plate. The fact that the screw can engage two cortices allowed the angle to be fixed. The fourth generation utilized a fixed angle countersunk screw in plate design as screw and plate mechanisms were continually used in smaller and more complex regions of the body. There was a need to be able to hold bony structures rigidly in situations where little inherent support was available. A fixed angle between the screw and plate was created by threading the head of the screw into the plate. The angle of the screw relative to the plate was determined at manufacture of the hardware. This technology is represented at least in part by U.S. Pat. No. 6,440,135, to Orbay et al.

One invention currently sold under the mark PEAK by DePuy Acromed (Raynham, Mass.) is disclosed in U.S. Pat. No. 5,954,722, to Bono. The apparatus described in this patent utilizes a plate with holes which have spherical diameter bores into which fit spherical outer diameter bushings. The bushings have a tapered, threaded inner diameter, and a specially designed screw is available that has a tapered head matching that of the bushing. As the screw is driven through the bushing, the threads engage and produce a radial force in the bushing, pushing against the inner wall of the plate. The alignment of the screw to the plate is held with a moment corresponding to the amount of friction between the bushing and the plate. Primary shortcomings of this apparatus include:
1. The angle of the screw must be determined prior to insertion of the screw.
2. The screw cannot optionally be allowed to remain unlocked as a locking construct must be used.
3. The locking mechanism requires careful planning upon insertion as long as there is propensity for "cross-threading" the construct due to its fine thread and long length.

4. Compression of bone with the screw independent of locking the screw in place is either not possible or is limited.

SUMMARY

As disclosed herein, novel systems and methods for bone fixation are provided in accordance with the present subject matter.

An object of the present disclosure is to provide novel and improved systems and methods for bone fixation. An object having been stated, and which is achieved in whole or in part by the present subject matter, other objects will become evident as the description proceeds when taken in connection with the accompanying drawings as best described hereinbelow.

BRIEF DESCRIPTION OF THE DRAWINGS

FIG. 5D of the drawings is a sectional view of the expander hub shown in FIG. 5C;

FIG. 9A of the drawings is a sectional view illustrating a portion of the fixation apparatus with the expander hub in an unlocked position;

FIGS. 11A-11C of the drawings are perspective views of drivers that can be used in association with the fixation apparatus shown in the previous figures;

DETAILED DESCRIPTION

In accordance with the subject matter disclosed herein, and with reference to the various figures of drawings, apparatuses, systems and methods are provided for fixating a fractured bone with the ability to establish and maintain accurate alignment and reduction of bone fragments as well as to maintain such reduction through the healing process. As described in detail hereinbelow, a fixation apparatus in accordance with the present disclosure can be utilized in association with a plate in order to achieve and maintain desired alignment, independent of the level of fixation, in order to facilitate healing of a bone fracture.

Figure 1:
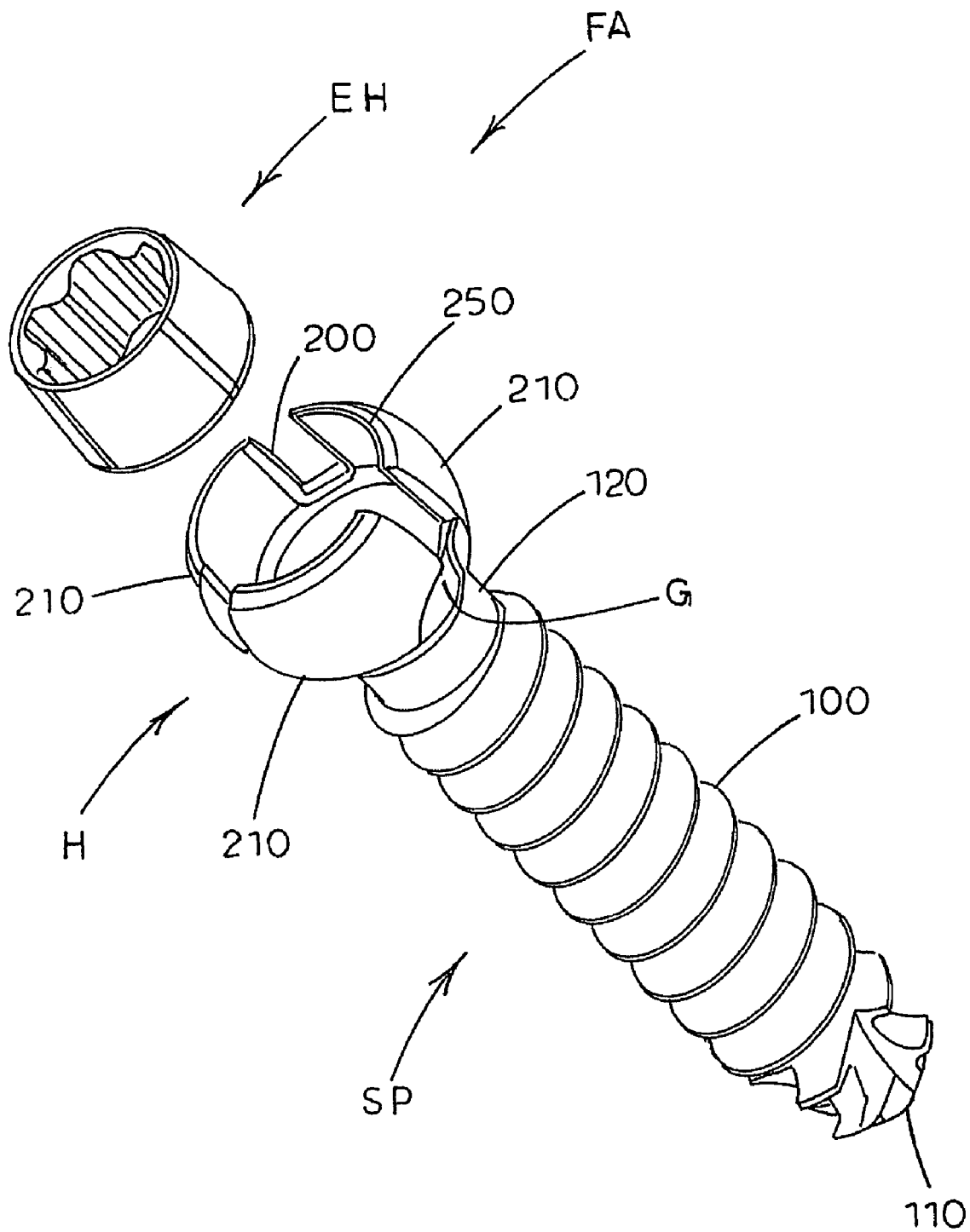
FIG. 1 of the drawings is a perspective view of an embodiment of a fixation apparatus with an expander hub shown detached.
Figure 2:
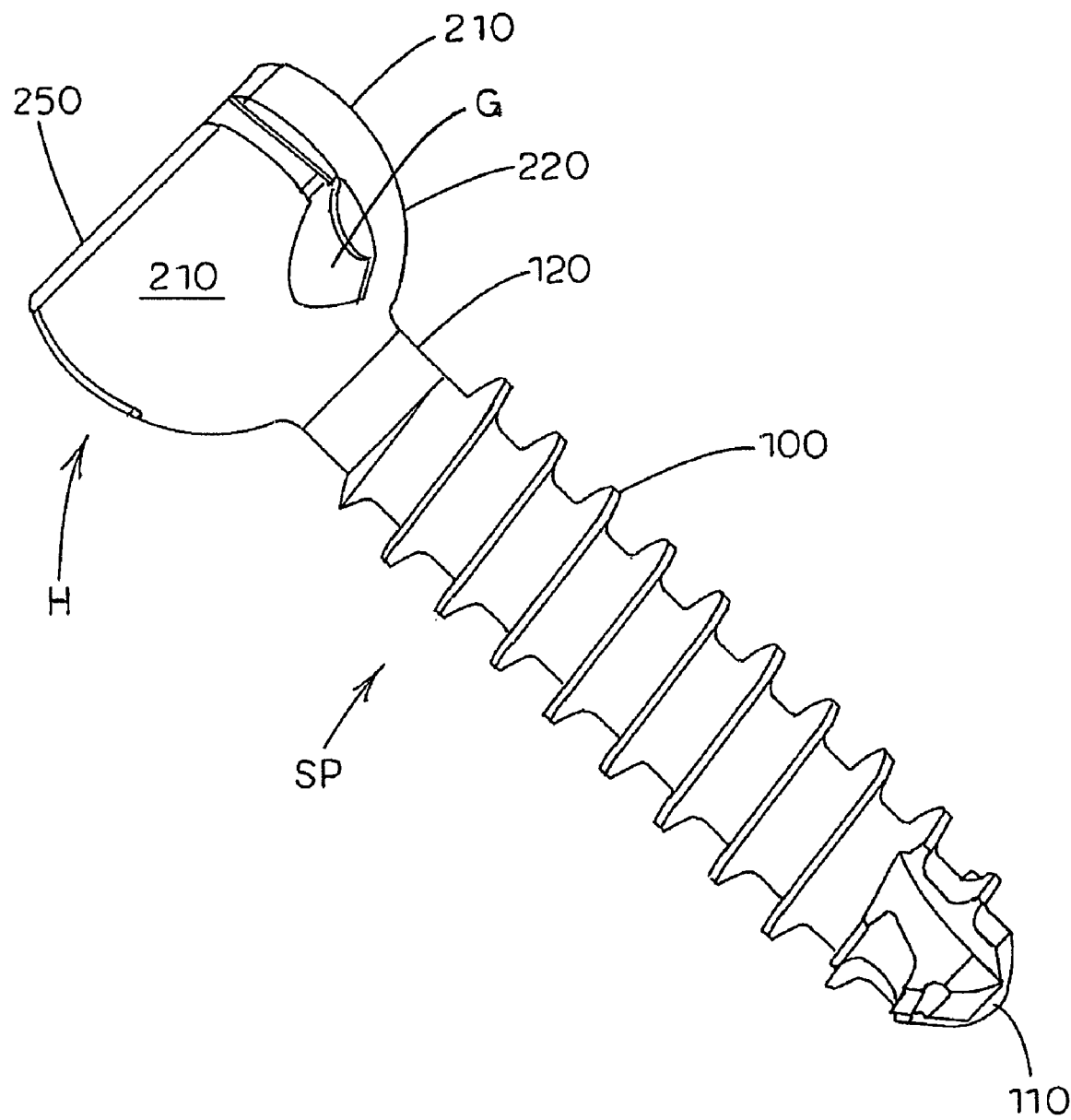
FIG. 2 of the drawings is a side view of the fixation apparatus shown in FIG. 1 without the expander hub.

Referring now to FIGS. 1 and 2 of the drawings, fixation apparatus generally designated FA is illustrated and comprises a head portion generally designated H which can have a shank portion generally designated SP extending therefrom. An expander hub generally designated EH is shown in FIG. 1 adapted for fitting into head portion H as described later in greater detail and as shown forth for illustration purposes in FIG. 1 detached from head portion H. As can be appreciated by those of skill in the art, shank portion SP can be formed as an integral part of and extension from head portion H or can separate and independent from head portion H.

Shank portion SP can be any suitable shank portion, threaded or unthreaded, and is illustrated in the drawings in one suitable, non-limiting configuration. As shown in FIGS. 1 and 2, a threaded shank portion SP of fixation apparatus FA can include any suitable type of thread, such as threads 100, along at least a portion of the length of shank portion SP and can also include a tip 110 which can be self-tapping, for facilitating screwing or otherwise placing fixation apparatus FA into bone. As can be appreciated by those of skill in the art, shank portion SP of fixation apparatus FA can be cannulated if desired and define an axial opening along the middle of shank portion SP Shank portion SP can be self-drilling and can be constructed of any suitable material known to those of skill in the art, such as, for example, titanium.

Head portion H of fixation apparatus FA can be integral with or separate from and attached to an end of shank portion SP opposite from the end of shank portion SP which includes tip 110. Head portion H can be of any suitable shape in accordance with the functionality described in the present disclosure and can be constructed of any suitable material known to those of skill in the art, such as, for example, titanium. One or more slots, such as slots 200 can be defined through portions of the wall of head portion H thereby creating wall sections 210 which are separated by slots 200 as illustrated, but that all extend from a base portion 220 of head portion H with base portion 220 being the part of head portion H closest to shank portion SP.

Expander hub EH of fixation apparatus FA can be of any suitable shape or configuration for functionality in accordance with the present disclosure as will be appreciated by those of skill in the art. As illustrated, expander hub EH is at least generally cylindrical in shape with a reverse, tapered outer diameter and an inclined, lower surface as described in greater detail hereinbelow. Expander hub EH can have a plurality of annular recesses and is adapted for fitting into a recessed portion of head portion H of fixation apparatus FA where it can be positioned in a disengaged or unlocked position wherein wall sections 210 of head portion H are not forced outwardly, and an engaged or locked position wherein wall sections 210 of head portion H are forced outwardly sufficient to lock fixation apparatus FA in a predetermined position as described further hereinbelow. As with the previous structures, expander hub EH can be constructed of any suitable material known to those of skill in the art, such as, for example, titanium.

As shown in FIGS. 1 and 2 (and FIG. 10 described below) of the drawings, head portion H can advantageously comprise a groove G that can be defined in the lower portion of head portion H and allows head portion H to be self-counterboring into bone. Screw heads with additional features, such as locking, can often be thicker than desired such that bone has to be countersunk to allow the screw head to sit in a thinner plate. This countersinking requires an additional step, therefore making the self-counterboring feature of head portion H quite advantageous.

Figure 3:
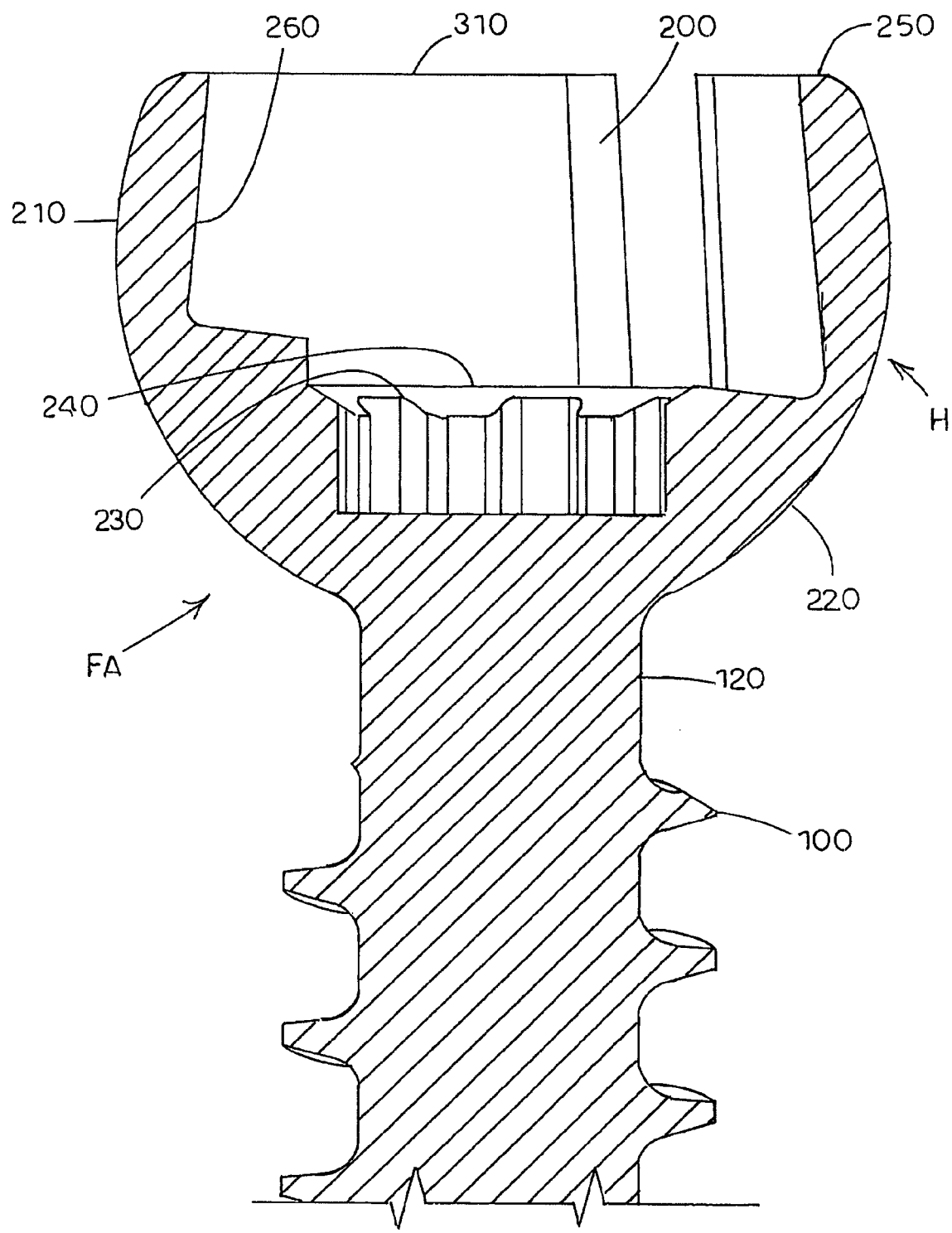
FIG. 3 of the drawings is a sectional view of an end portion of the fixation apparatus shown in FIG. 2.
Figure 4:
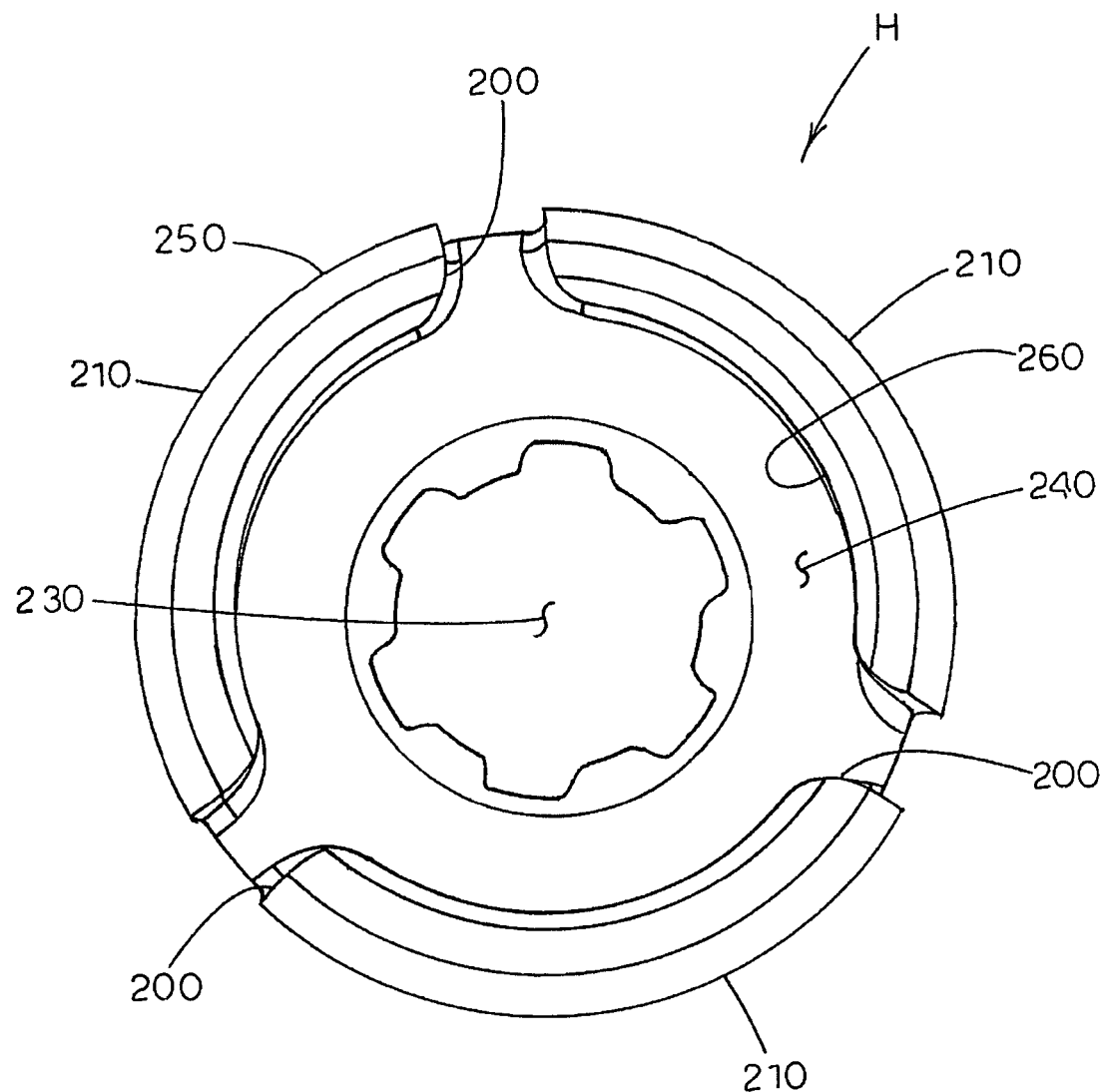
FIG. 4 of the drawings is an end view of the fixation apparatus shown in FIG. 2.

Referring now to FIG. 3 of the drawings, a cross-sectional view of head portion. H and shank portion SP of fixation apparatus FA is illustrated. Expander hub EH is not present in FIG. 3. Shank portion SP can be of any suitable design with outer threads 100 adapted for screwing into bone. Head portion HP, however, advantageously comprises slot 200, wall sections 210 and base portion 220 as illustrated in FIG. 3 wherein base portion 220 includes a recess designated 230. Recess 230 is perhaps best illustrated in FIGS. 3 and 4 of the drawings and can be of any suitable shape or configuration adapted for receiving a driver in order to rotatably drive head portion H and shank portion SP when present and when desired such as when shank portion SP is threaded for screwing shank portion SP into bone. As shown in FIG. 4, recess 230 of base portion 220 defines a hexagonal configuration adapted to receive a suitably shaped driver with a matching hexagonal end for being matingly received into recess 230 for rotatably driving head portion H and shank portion SP.

Still referring to FIGS. 3 and 4 primarily, recess 230 of base portion 220 is advantageously defined in an upper surface 240 of base portion 220 of head portion H. Upper surface 240 is preferably slightly inclined from one side of head portion H to the other as illustrated in FIG. 3 to facilitate the locking feature of expander hub EH (shown in FIG. 1) when positioned in head portion H as described further hereinbelow. The hollow or recessed portion of head portion H at least partially surrounded by wall sections 210 can be of a larger diameter at the bottom thereof (at upper surface 240 of base portion 220) than at the top end 250 of head portion H. To achieve this feature, the inner portions or sides 260 of wall sections 210 facing the interior of head portion H can have a reverse taper and extend gradually further inwardly the further they extend from upper surface 240 of base portion 220. Slots 200 of head portion H as illustrated in FIG. 3 can be defined from top end 250 of head portion H to base portion 220 and extend along a line that is at least generally parallel to a longitudinal, central axis of shank portion SP. Groove G (shown in FIGS. 1 and 2) can be defined in the lower portion of head portion H below slots 200 of head portion H in order for head portion H to be self-counterboring into bone FIGS. 5A, 5B, 5C and 5D of the drawings illustrate expander hub EH which is adapted to fit into the recessed portion of head portion H at least partially surrounded by wall sections 210 above base portion 220. Expander hub EH can be at least generally cylindrical in shape and have a reverse tapered outer diameter such that the outer diameter of expander hub EH is greater at its bottom or lowest surface 300 than the outer diameter of expander hub EH at the opposite uppermost surface 310. Expander hub EH includes an outer wall 320 which can optionally comprise one or more lobes, such as lobes 330, three of which are shown on expander hub EH in the disclosed embodiments. Lobes 330 can be formed as expanded bands or portions of outer wall 320 and can be spaced-apart equally on outer wall 320.

Figure 5A:
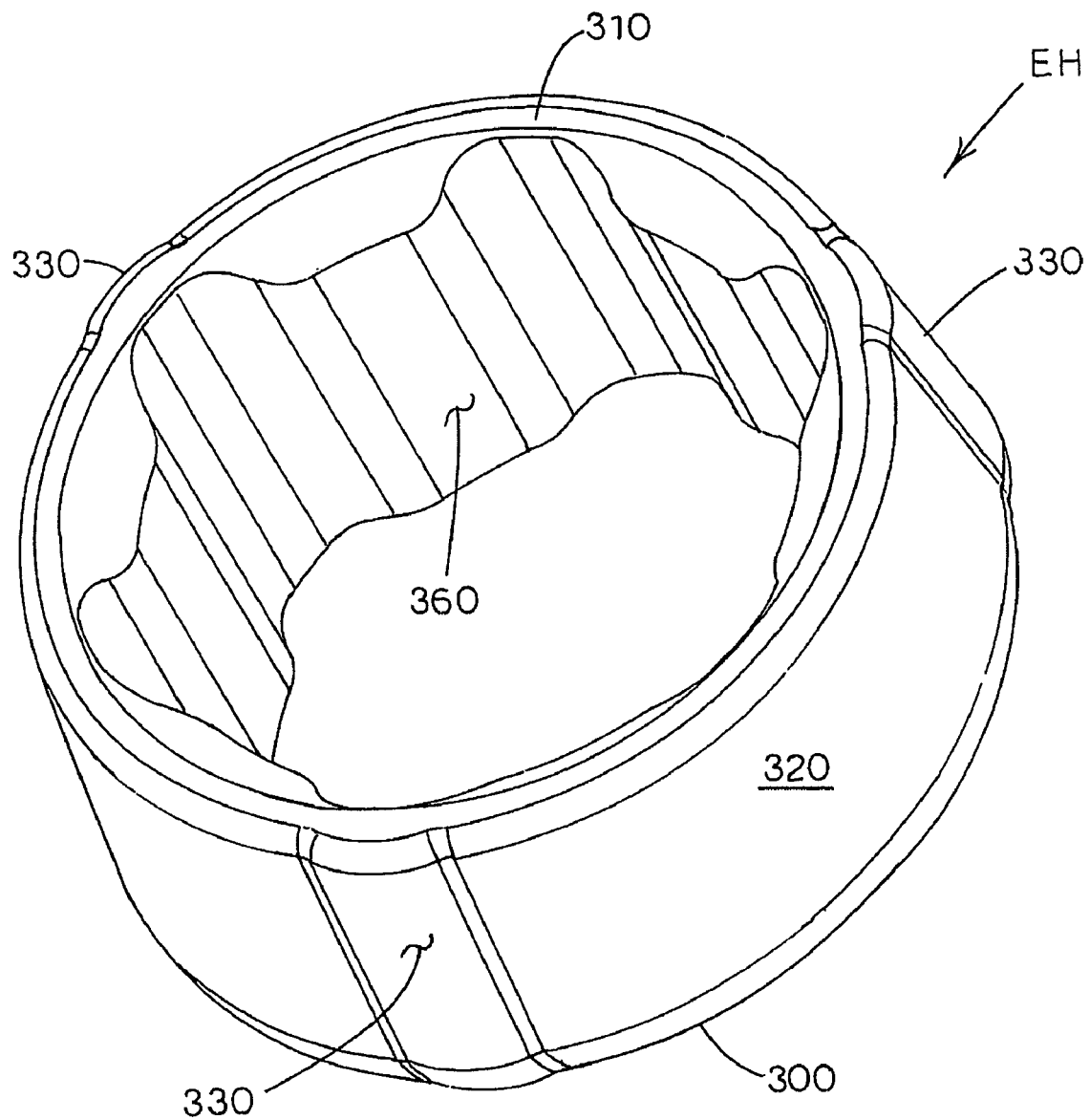
FIG. 5A of the drawings is a perspective view of the expander hub shown in FIG. 1.
Figure 5B:
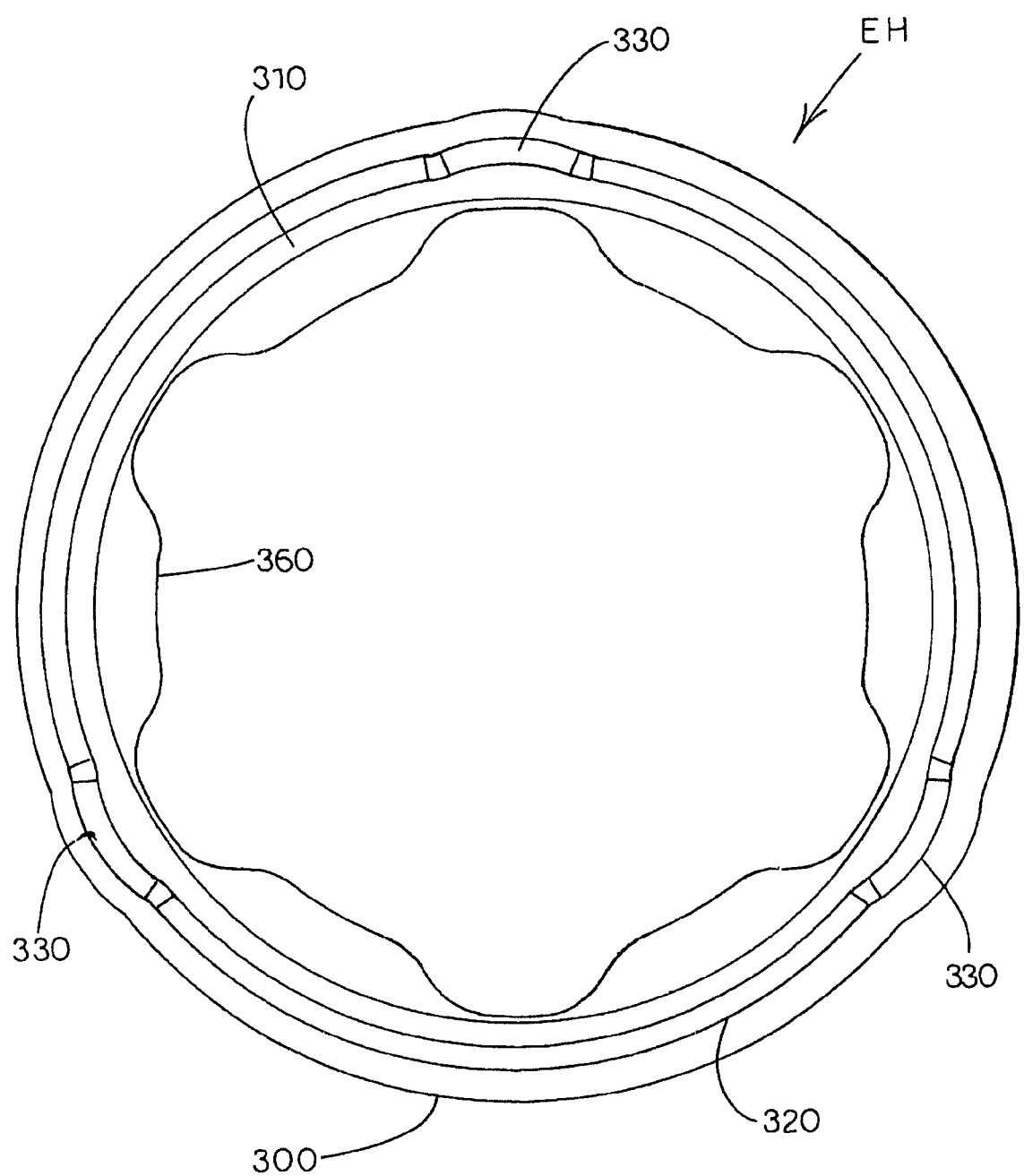
FIG. 5B of the drawings is a top plan view of the expander hub shown in FIG. 1.
Figure 5C:
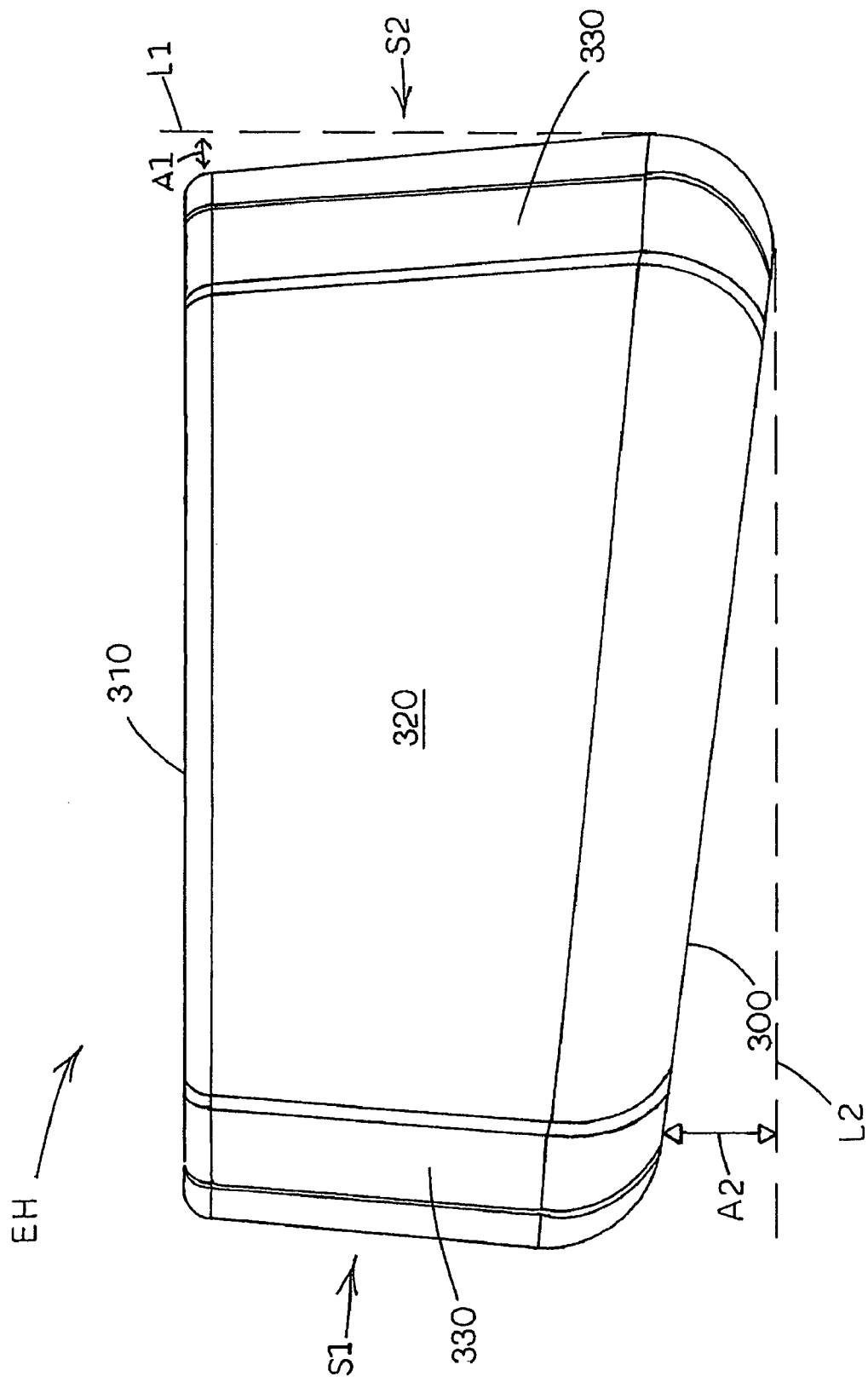
FIG. 5C of the drawings is a side elevation view of the expander hub shown in FIG. 1.

When present, lobes 330 can each extend radially past the outer diameter of expander hub EH that is defined by outer wall 320, and lobes 330 can extend from the uppermost surface 310 of expander hub EH to the lowest surface 300 of expander hub EH. As illustrated in FIGS. 5A-5D, the outer diameter of expander hub EH at uppermost surface 310 is less than the outermost diameter of expander hub EH at lowest surface 300. Outer wall 320 extends between uppermost surface 310 and lowest surface 300 wherein outer wall 320 can be aligned as illustrated in FIG. 5C at an angle A1 of from at least about 2° to 8° from a vertical line designated in phantom as line L1.

As best illustrated in FIGS. 5C and 5D of the drawings, lowest surface 300 of expander hub EH can extend along a line that is not parallel with the line along which uppermost surface 310 extends. Instead, expander hub EH can include a short side generally designated S1 and a long side generally designated S2 with uppermost surface 310 extending therebetween along a line which is at least substantially horizontal but with lowest surface 300 extending along a line therebetween which can be at an angle A2 of from about at least 6° to 12° from line L2, which is parallel to uppermost surface 310 as illustrated in FIGS. 5C and 5D.

The inner diameter of expander hub EH can be of any suitable shape designed for receiving a driver in order to rotate expander hub EH. As illustrated particularly in FIGS. 5A, 5B and partially in FIG. 5D, expander hub EH includes an inner wall 360 which defines an opening through the center of expander hub EH and which can be fixed or moveable inwardly or outwardly. Inner wall 360 forms a shape adapted for receiving a driver for rotating driving expander hub EH. As shown, inner wall 360 forms a hexagonal recess adapted for receiving a driver with a matching hexagonal driving end for rotating expander hub EH. As can be appreciated by those of skill in the art, any suitable shape can be formed by inner wall 360 in order to suitably rotate expander hub EH. As can be appreciated further hereinafter, a driver for fitting into recess 230 of base portion 220 of head portion H can be inserted through the middle of expander hub EH in order to rotate head portion H into shank portion SP as can be appreciated by those of skill in the art. To facilitate such a feature, recess 230 of head portion H can be smaller in diametrical size as compared with the central opening defined by inner wall 360 of expander hub EH.

Figure 6:
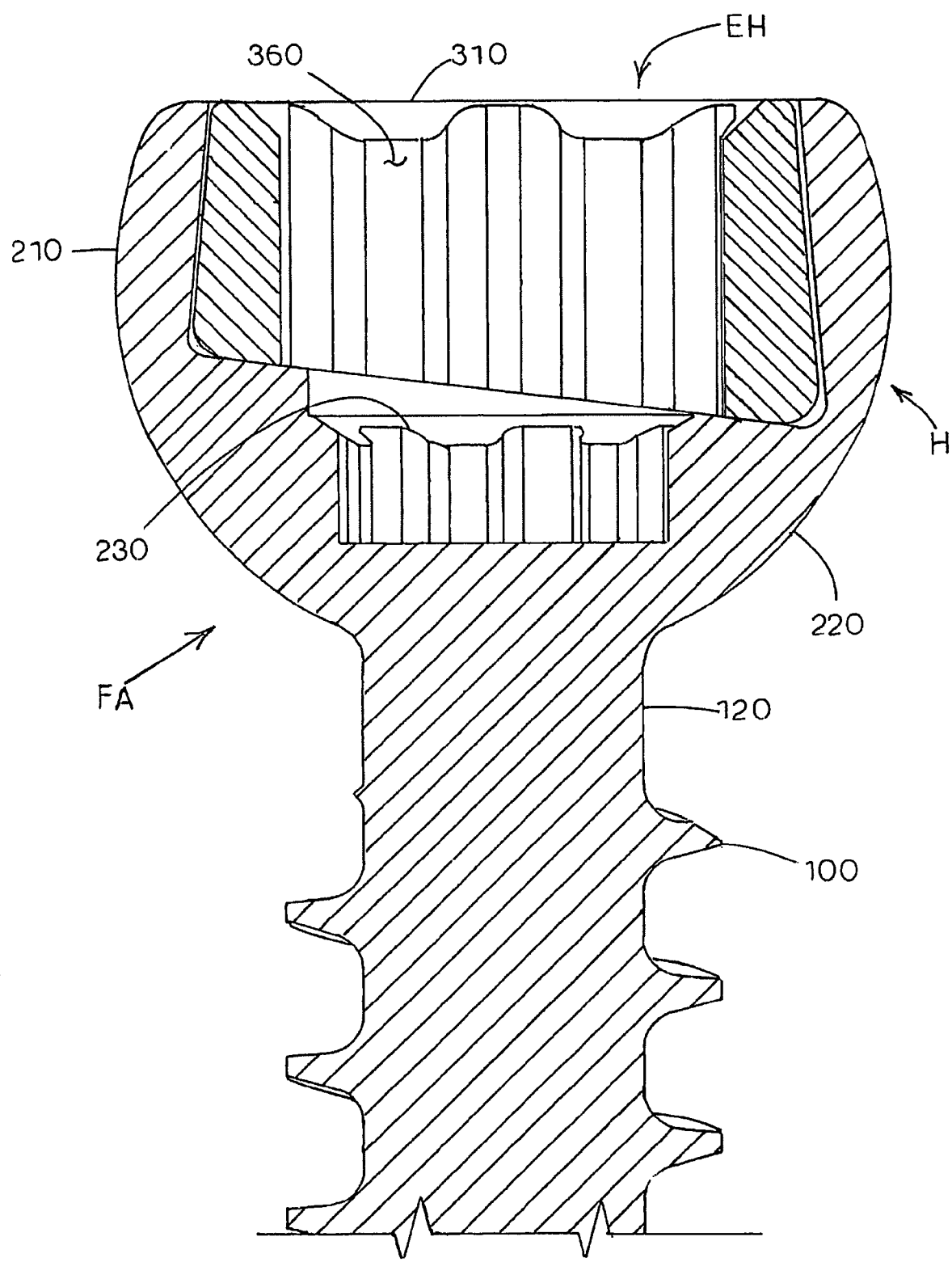
FIG. 6 of the drawings is a sectional view of an end portion of the fixation apparatus of Figure shown in FIG. 2 with the expander hub in place.
Figure 7A:
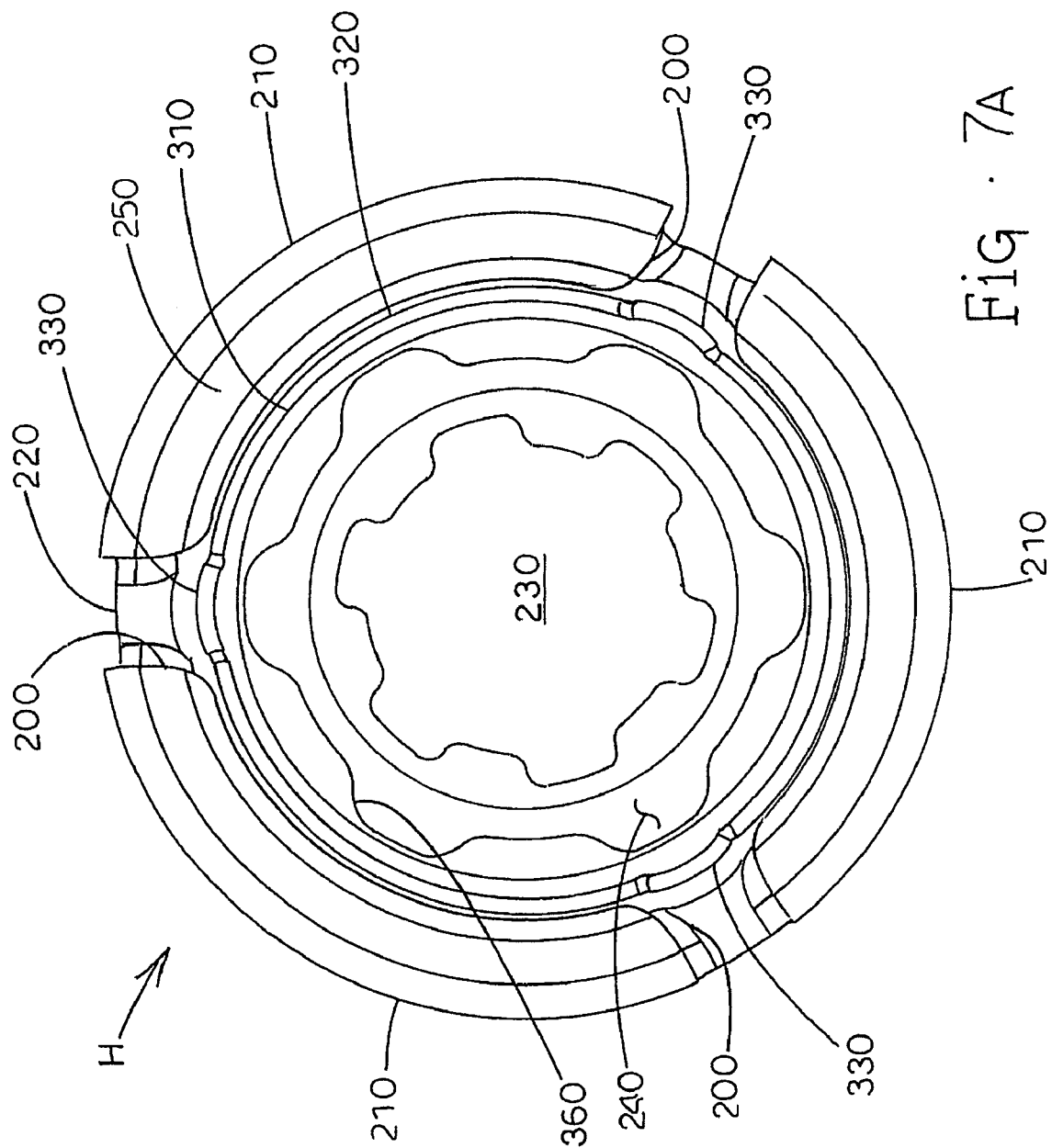
FIG. 7A-7C of the drawings are end views of the head portion of the fixation apparatus shown in FIG. 6 illustrating various positions of the expander hub.

FIG. 6 illustrates expander hub EH positioned within head portion H of fixation apparatus FA. As shown, expander hub EH is in what is referred to herein as an unlocked position, wherein the lowest surface of expander hub EH is at least substantially flat against upper surface 240 of head portion H. In this position, there is little or no pressure exerted by outer wall 320 of expander hub EH against inside 260 of head portion H. As shown, uppermost surface 310 of expander hub EH is at least substantially at the level of top end 250 of head portion H of fixation apparatus FA. FIG. 7A also illustrates expander hub EH in this unlocked position providing a top, plan view of expander hub EH within head portion H of fixation apparatus FA. Although lobes 330 are considered optional and not necessary for locking of fixation apparatus FA, when present, lobes 330 of expander hub EH can be aligned with slots 220 of head portion H in the unlocked position shown in FIG. 7A. FIG. 9A illustrates fixation apparatus FA positioned through a hole 400 of a plate P with expander hub EH in this unlocked position.

Figure 7B:
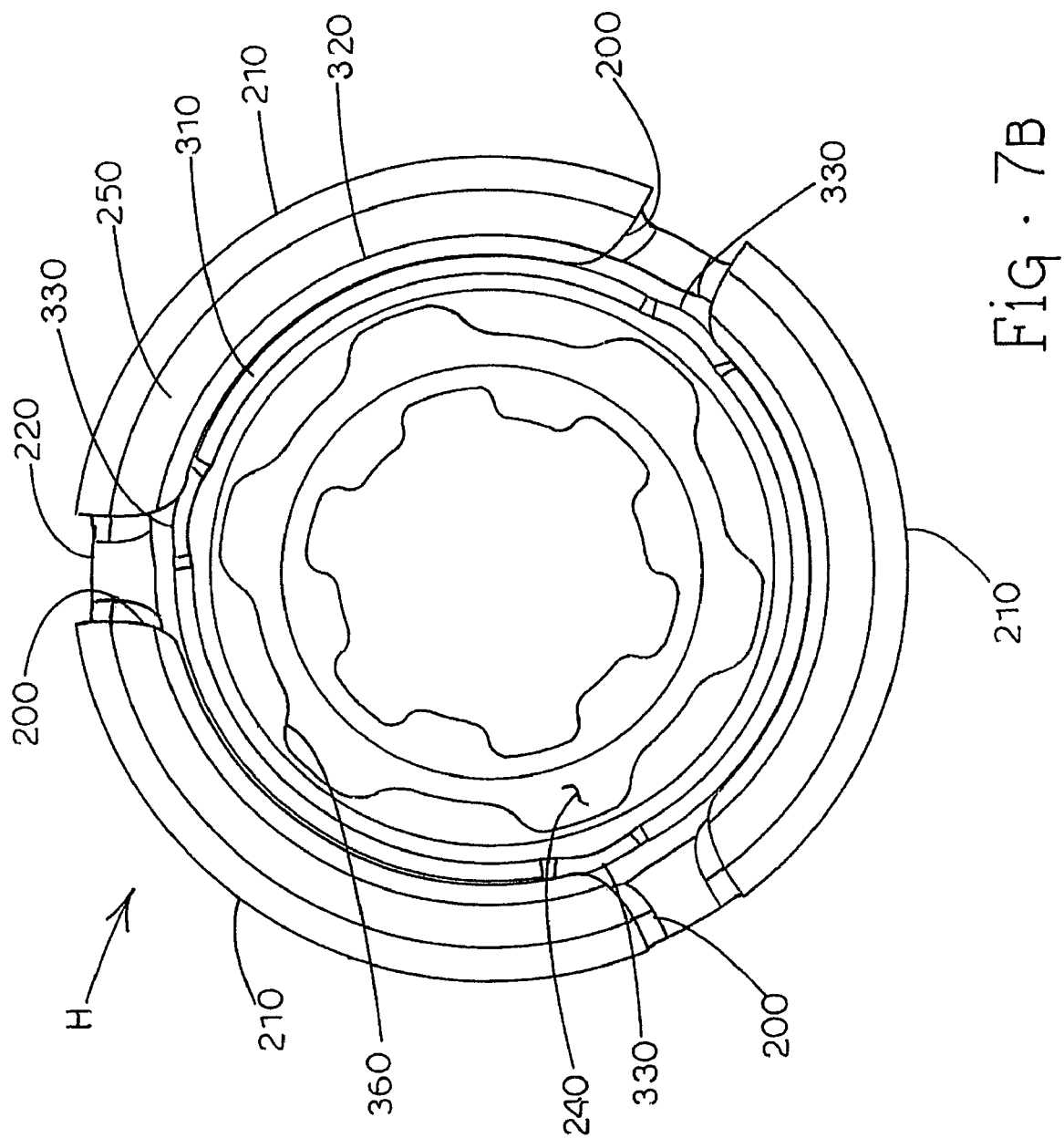

From the position shown in FIGS. 6 and 7, expander hub EH can be locked in position in head portion H by simply suitably rotating expander hub EH. FIG. 7B illustrates initiation of this locking process as expander hub EH has been rotated in a clockwise direction within head portion H. Although optional, lobes 330 as shown when present in FIG. 7B move out of alignment with slots 220 and can begin to exert pressure against wall sections 210 of head portion H.

Figure 7C:
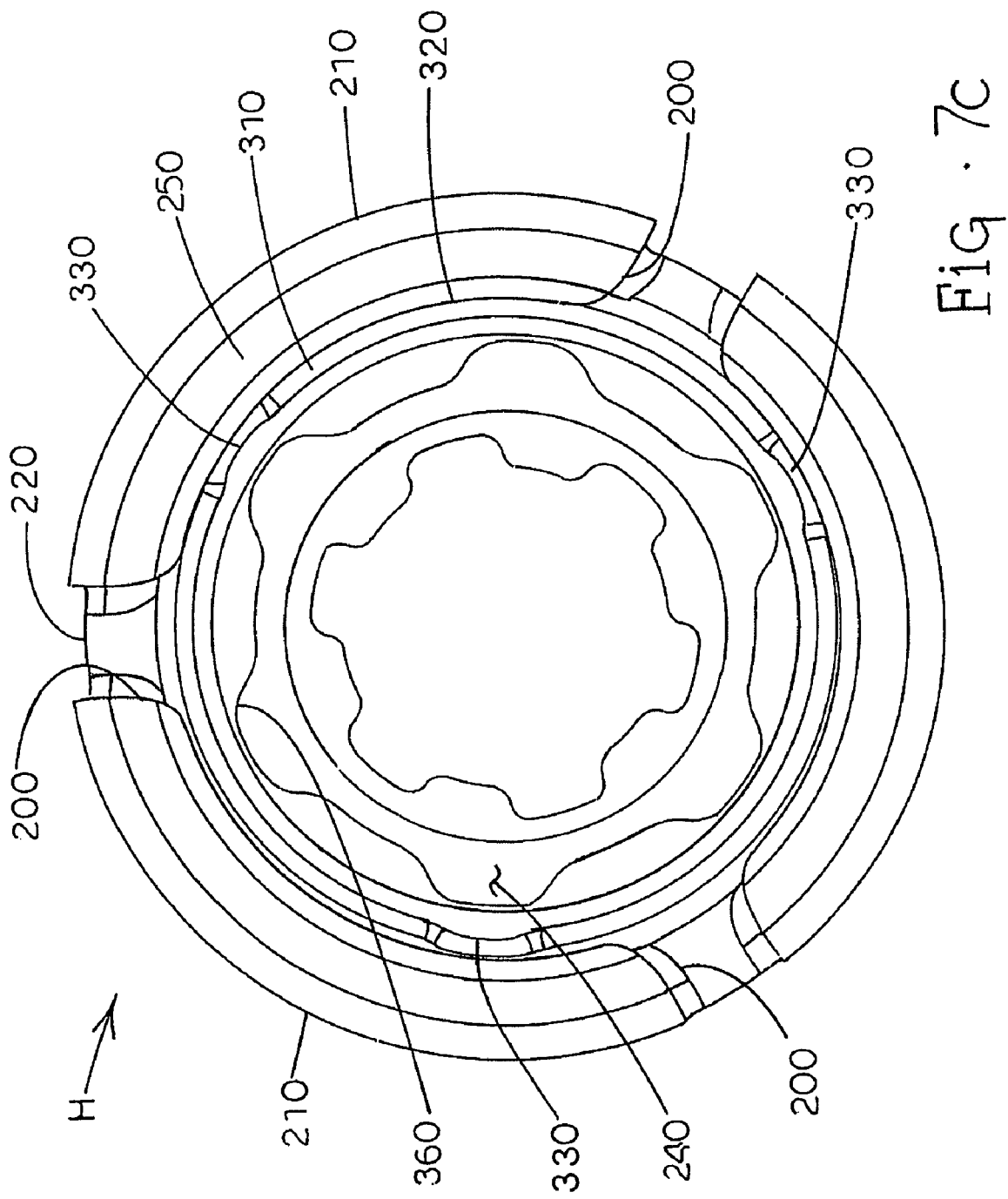

FIG. 7C illustrates expander hub EH locked in position within head portion H as expander hub EH has been rotated even further from its position shown in FIG. 7B wherein lobes 330 are further away from slots 220 and press against wall sections 210 of head portion H. As shown with the disclosed configuration, each one of wall sections 210 has one of lobes 330 exerting outward force against it. In this manner, wall sections 210 of head portion H can be forced to move outwardly sufficient to press wall sections against any structure receiving fixation apparatus FA, as further described hereinbelow.

Figure 8:
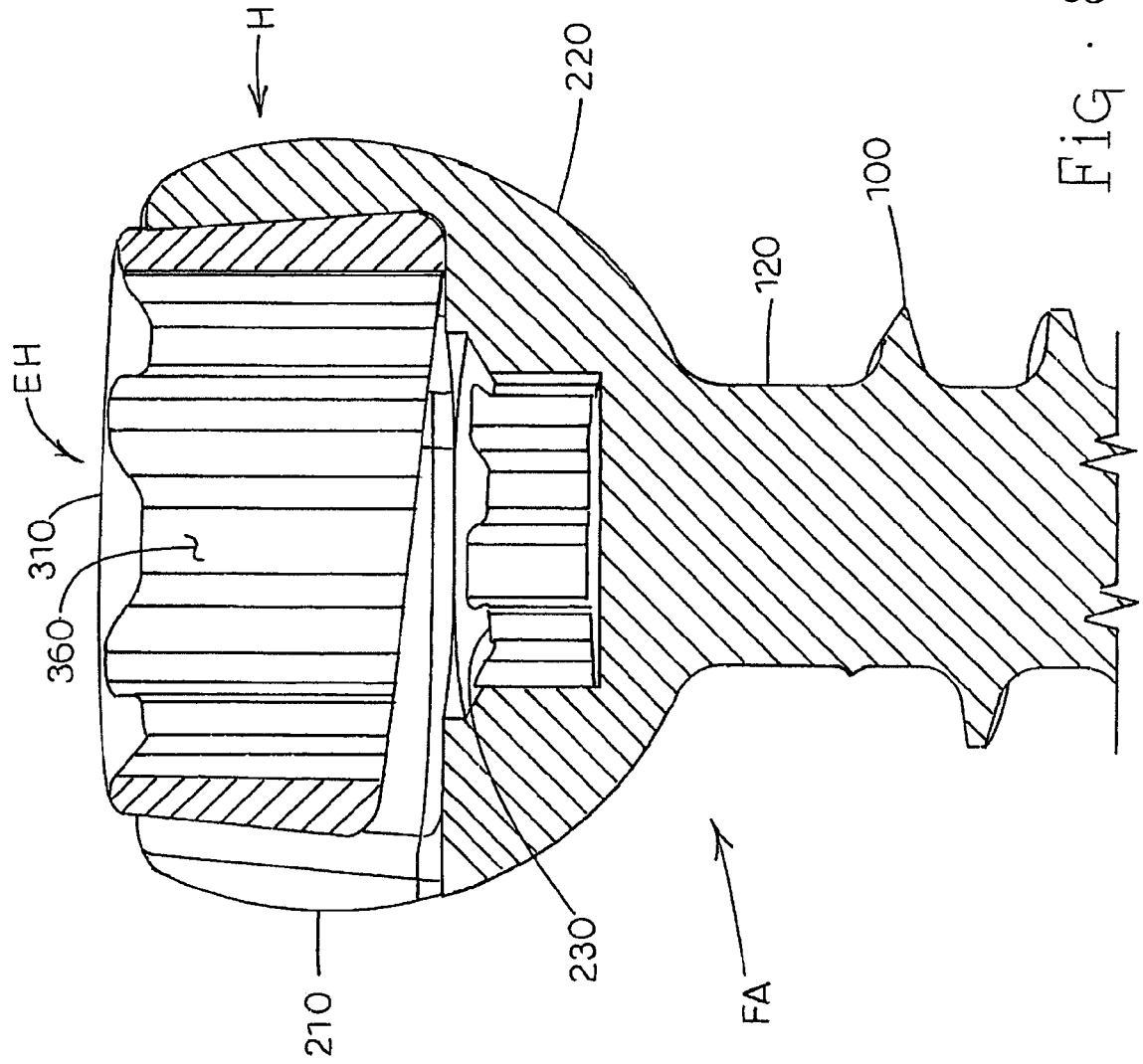
FIG. 8 of the drawings is a sectional view of and end portion of the fixation apparatus of FIG. 6 illustrating the expander hub in a locked position.

FIG. 8 of the drawings also illustrates expander hub EH in the locked position shown in FIG. 7C, but from a cross-sectional viewpoint. As shown, the rotation of expander hub EH to reach this locked position has vertically raised expander hub EH within head portion H such that uppermost surface 310 of expander hub EH is now higher than the level of top end 250 of head portion H of fixation apparatus FA. This elevation of expander hub EH results due to the incline or taper of upper surface 240 of head portion H and the incline of lowest surface 300 of expander hub EH. Since these inclined surfaces at least substantially match to allow expander hub EH to rest or fit at least like a puzzle piece against upper surface 240 of head portion H when in the unlocked position, rotation of expander hub EH to the locked position as described understandably raises expander hub EH as shown as the inclined surfaces of upper surface 240 and lowest surface 300 move away from this fitted position.

The reverse taper of inside 260 of wall sections 210 of head portion H facilitates retaining expander hub EH within head portion H as expander hub EH changes elevation relative to head portion H. The incline or taper of outer wall 320 of expander hub EH is designed for cooperation with this reverse taper feature to allow desirable movement of expander hub EH. The vertical or rising movement of expander hub EH within head portion H caused by rotation of expander hub EH causes outer wall 320 of expander hub EH, by its greater lower diameter and gradually decreasing upper diameter, to exert force on inside 260 of wall sections 210 of head portion H to force wall sections 210 outwardly, especially when inside 260 of wall sections 210 has a gradual incline or taper opposite from outer wall 320 of expander hub EH.

Figure 9B:
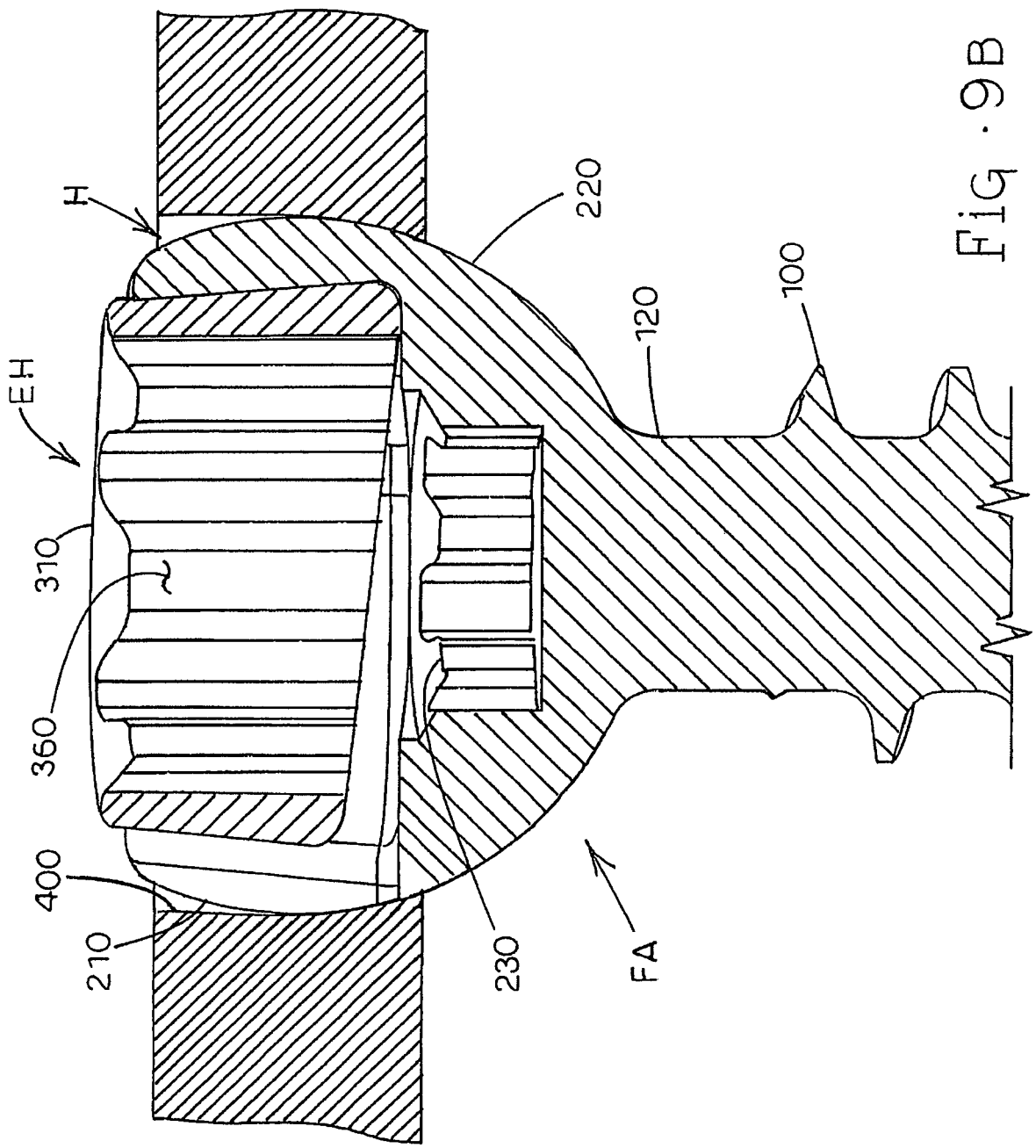
FIG. 9B of the drawings is a sectional view illustrating a portion of the fixation apparatus with the expander hub in a locked position.

FIGS. 9A and 9B of the drawings show a close-up view of fixation apparatus FA positioned through hole 400 of plate P. Expander hub EH is in an unlocked position in FIG. 9A where little or no pressure is exerted by wall sections 210 of head portion H against the inner wall of hole 400 of plate P to hold or maintain fixation apparatus FA in any specific position or alignment. Expander hub EH is in its locked position in FIG. 9B where wall sections 210 of head portion H are forced outwardly by expander hub EH to exert sufficient pressure against the inner wall of hole 400 to maintain and lock fixation apparatus FA in a desired position and alignment it extends through hole 400 of plate P. Sufficient pressure can exist plate P to lock fixation apparatus FA in position where the angle at which fixation apparatus FA is positioned through and within hole 400 of plate P can also be fixed and locked.

Figure 10:
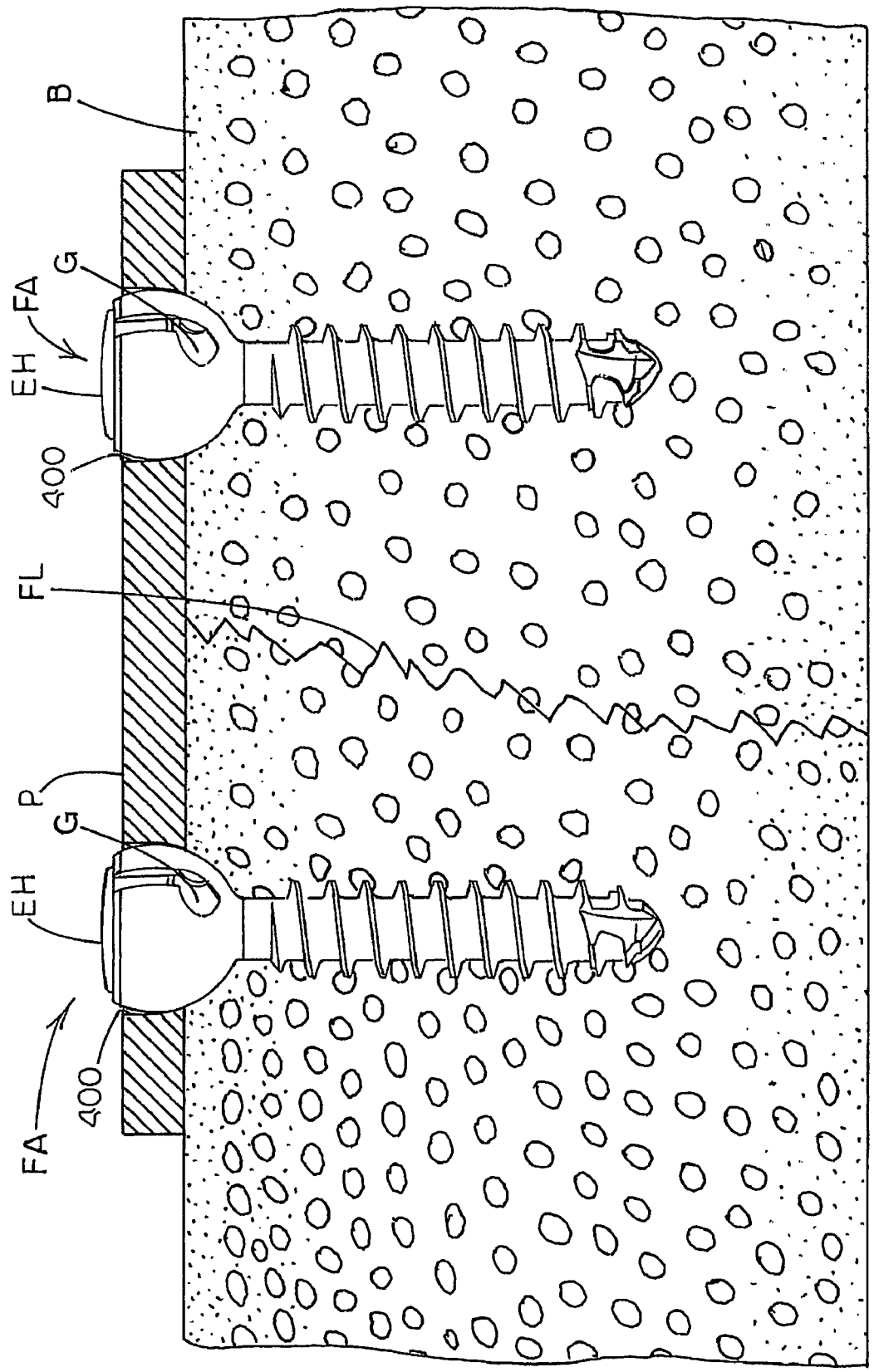
FIG. 10 of the drawings is a sectional view illustrating two fixation apparatuses locked in place against a plate to fixate a fracture.
Figure 12C:
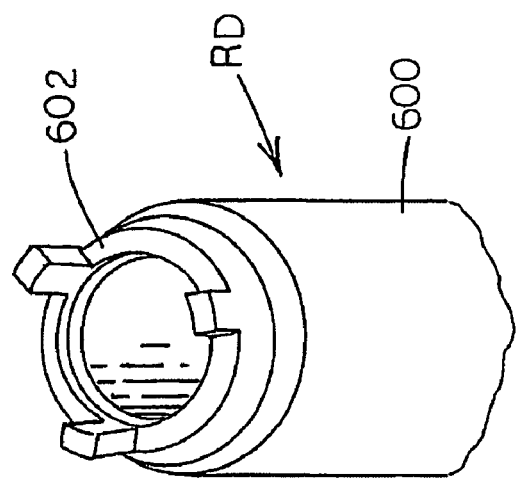
FIG. 12A-12C of the drawings are perspective views of the head portions of the drivers of FIGS. 11A, 11B and 11C, respectively.
Figure 12B:
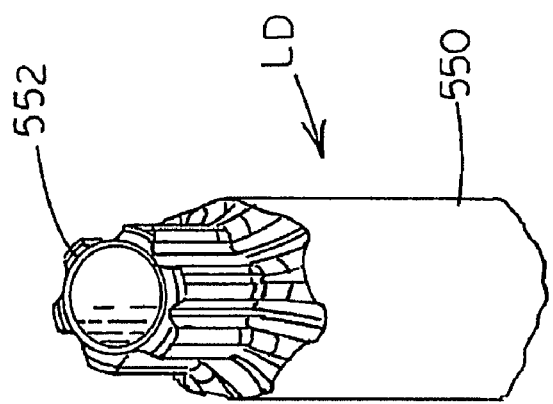
Figure 12A:
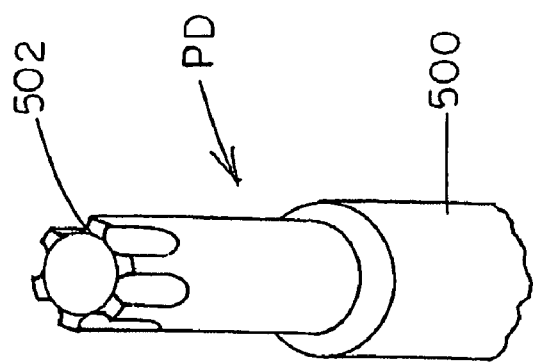

FIG. 10 illustrates, for exemplary purposes and without limitation, two identical fixation apparatuses FA extending through holes H of plate P and partially into bone B. Plate P extends across a bone fracture line FL and is held in position there to fixate fracture line FL. As can be appreciated by those of skill in the art, any suitable number of fixation apparatuses could be used with any suitable configuration of holes and plates as may be desired depending upon the situation. It is envisioned of course that one or more plates such as plate P can be utilized with one or more fixation apparatuses FA, and that fixation apparatuses FA can be locked into any suitable position or alignment to fixating a fracture. For example, fixation apparatuses FA may extend through material other than bone immediately under a hole 400, such as through soft tissue or other non-bone material. As shown in FIG. 10, groove G of each fixation apparatus FA has allowed each head portion H to self-counterbore into bone B so as to be below the upper surface of bone B.

While any suitable drivers could be used in association with the subject matter described herein, FIGS. 11A, 11B, 11C, 12A, 12B, and 12C, 13 and 14 illustrate, without limitation, exemplary embodiments of drivers that can be used. Placement driver PD is shown generally designated in FIGS. 11A, 12A, 13 and 14 and can be used to drive fixation apparatus FA into suitable material such as bone. Placement driver PD can be elongated and include a shaft portion 500 terminating in an end 502 configured to mate with recess 230 (FIGS. 3 and 4) within head portion H. As shown, end 502 comprises a hexagonal shape to at least substantially matingly engage recess 230. In this manner, rotation of placement driver PD forces likewise rotation of fixation apparatus FA. Any suitable material of construction can be used for placement driver PD, such as, for example, titanium.

Locking driver LD is shown generally designated in FIGS. 11B, 12B, 13 and 14 and can be used to lock expander hub EH. Locking driver LD can be elongated and cannulated to fit over at least a portion of placement driver PD as further described hereinbelow. Locking driver LD preferably includes a shaft 550 and terminates in one end 552 which is configured to be inserted into the middle of expander hub EH to matingly engage inner wall 360. In this manner, rotation of locking driver LD forces likewise rotation of expander hub EH. Any suitable material of construction can be used for locking driver LD, such as, for example, titanium.

When shank portion SP is connected to head portion H, rescue driver RD is shown generally designated in FIGS. 11C, 12C, 13 and 14 and can be used to stop rotation of head portion H. This function of rescue driver RD is not necessary when shank portion SP is part of or connected with head portion H. Rescue driver RD can be elongated and cannulated to fit over at least a portion of locking driver LD as further described hereinbelow. Rescue driver RD preferably includes a shaft 600 terminating in an end which can include tabs 602. Rescue driver RD can be configured to be inserted into slots 200 of head portion H. In this manner, rotation of rescue driver RD limits rotation of head portion H during locking. A handle 604 can be attached to the end of rescue driver RD opposite end 602 and used for gripping to apply rotational force to rescue driver RD. Any suitable material of construction can be used for rescue driver RD, such as, for example, titanium.

Figure 13:
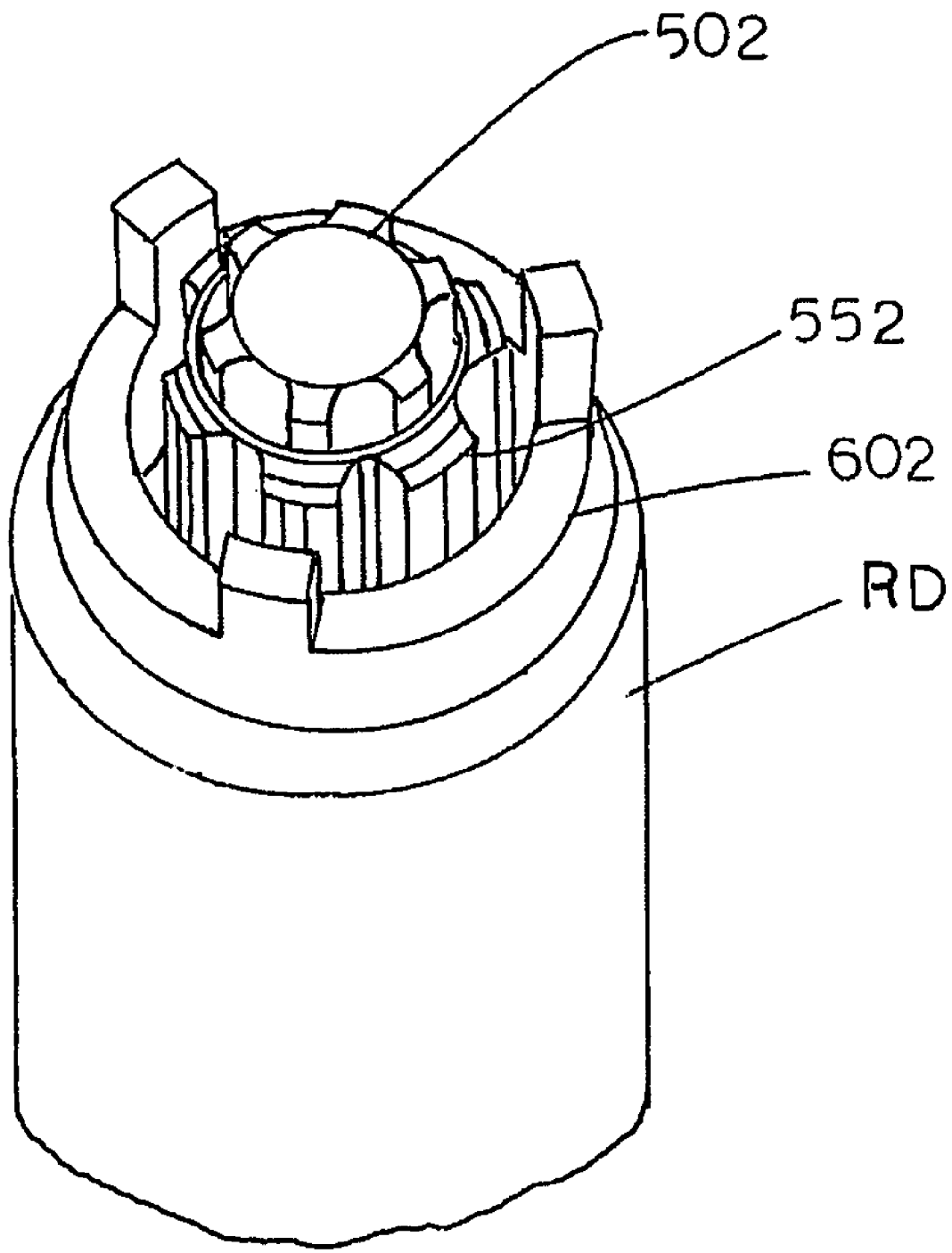
FIG. 13 of the drawings is a perspective view of the drivers of FIGS. 11A-11C and 12A-12C assembled together for use.
Figure 14:
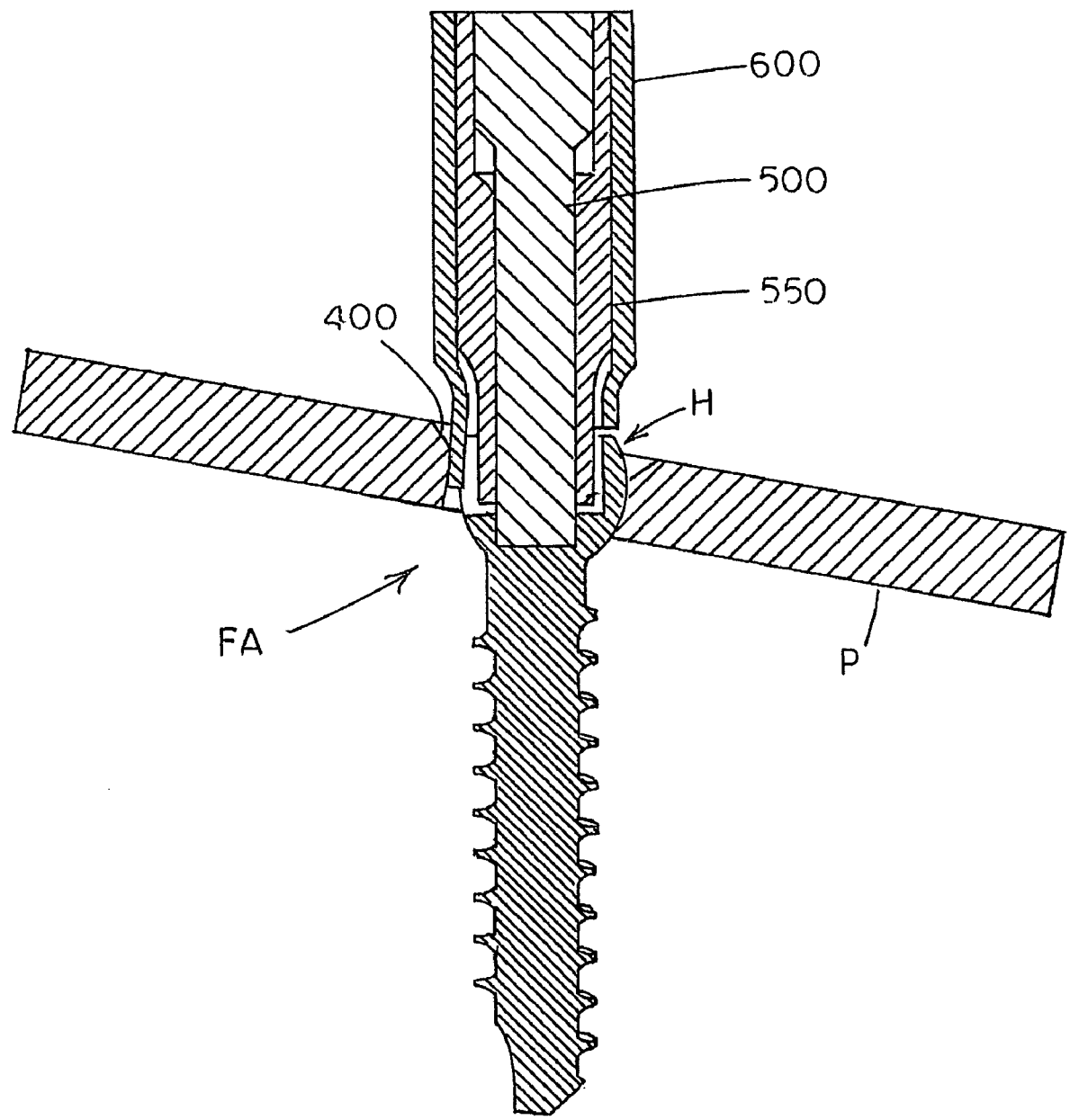
FIG. 14 of the drawings is a sectional view of the assembly of drivers of FIG. 13 positioned against the fixation apparatus for use.

FIG. 13 illustrates a nested and concentric configuration for the drivers shown in FIGS. 11A-12C, and FIG. 14 illustrates the nested configuration of drivers in contact with fixation apparatus FA which extends through hole 400 of plate P. Placement driver PD is shown at the center, with locking driver LD positioned over or around placement driver PD, but with end 500 of placement driver PD extending farther that end 550 of locking driver LD. Rescue driver RD is positioned over or around locking driver LD as shown. From this configuration, and as can be readily appreciated by those of skill in the art, the drivers can be used in cooperation with one another without having to remove each before using another.

Exemplary Method of Use

It is envisioned that a fixation apparatus FA with the expander hub as disclosed herein could be used in any manner known to those of skill in the art based upon the present disclosure. When utilized for fixating a bone fracture, as a non-limiting example, a surgeon can be presented with any suitable plate, such as plate P (such as shown in FIGS. 9A, 9B, 10 and 14) for affixing across a bone fracture and a screw. Plate P can be provided with any suitable configuration of holes defined therethrough, such as hole 400 for receiving fixation apparatus FA. The shape and size of hole 400 can be of any suitable shape and size, such as spherical, as can be appreciated by those of skill in the art. Expander hub EH can be positioned (without being locked) in head portion H of fixation apparatus FA prior to packaging.

Plate P can be placed over an appropriate bone site, such as above and/or across a fracture line FL, as shown for example in FIG. 10, using any suitable driver, such as placement driver PD shown in FIGS. 11A, 12A, 13 and 14. By applying rotational pressure to placement driver PD, fixation apparatus FA can be driven into bone. As head portion H of fixation apparatus FA passes through the entrance to hole 400 in plate P, the smaller outer diameter of expander hub EH, and, when present, lobes 330 resting within slots 200 of fixation apparatus FA, allow slots 200 to narrow, and the outer diameter of fixation apparatus FA to compress and slide through the opening of hole 400. Fixation apparatus FA can continue to be driven by placement driver PD until sufficient "lag" compression is obtained between plate P and head portion H of fixation apparatus FA. At this point, fixation apparatus FA can rotate relative to plate P about the center of hole 400.

Once fixation apparatus FA is positioned and suitably driven into bone B through hole 400 by placement driver PD, locking driver LD can be used, without removing placement driver PD so as to hold fixation apparatus FA stationary, to rotate expander hub EH within head portion H of fixation apparatus FA to lock expander hub EH and thereby lock in place fixation apparatus FA. For this "locking" to occur, first lobes 330, when present, of head portion H engage, with interference, inside 260 of wall sections 210 of head portion H. The rotation also causes the inclination of upper surface 240 within head portion H and that of lowest surface 300 of expander hub EH to force expander hub EH to elevationally and axially move upward within head portion H of fixation apparatus FA. This movement engages the tapered surface of outer wall 320 of expander hub EH and that of inside 260 of wall sections 210 of head portion H further creating a radial, outward pressure on inside 260 of wall sections 210 of head portion H. The outer diameter of fixation apparatus FA is thereby expanded, interfering with the inner diameter of the hole, such as hole 400, of plate P, and creating friction, which locks the angle and alignment of fixation apparatus FA in place through hole 400. Fixation apparatus FA can advantageously be used with P plate whereby fixation apparatus FA and plate P can compress bone separately from locking the fixation apparatus in a desired position. Also, the angle, alignment or position of fixation apparatus FA can be changed if desired even after locking of fixation apparatus FA.

It can therefore be seen that the angle and alignment of the fixation apparatus can be adjusted after placement of fixation apparatus FA, but prior to locking. This advantageously allows the position of fixation apparatus FA to be aligned using the angle of fixation apparatus FA, and advantageously allows fixation apparatus FA to be held in place with the locking aspect as described. Locking of fixation apparatus FA is optional and is not a necessary step for fixating a bone fracture. By nature of the design, expander hub EH cannot come free from the head portion of fixation apparatus FA, thus avoiding the potential introduction of a free foreign body under the skin. Even if expander hub EH were to become unlocked or disengaged after locking, the system as disclosed herein would continue to function as well as conventional bone fixation systems. With fixation apparatus FA locked in place as described herein, three potential undesirable failures of conventional fixation apparatus systems that are avoided include torsional back-out, change of the angle of the fixation apparatus, and pull-out of the fixation apparatus.

Figure 15:
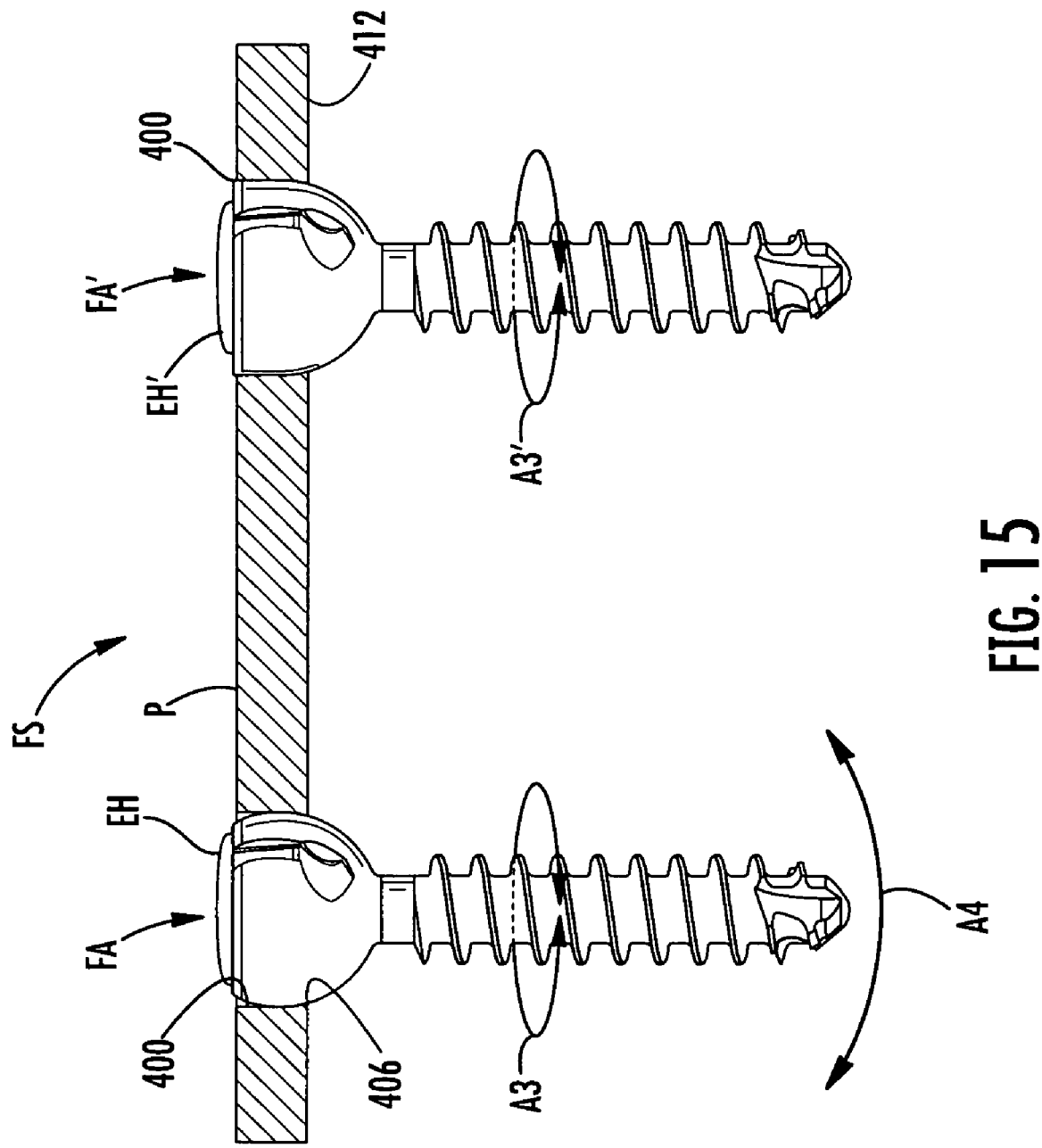
FIG. 15 of the drawings is a sectional view illustrating a fixation system including a laterally-fixed fixation apparatus and a laterally-variable fixation apparatus locked in place against a plate.
Figure 16:
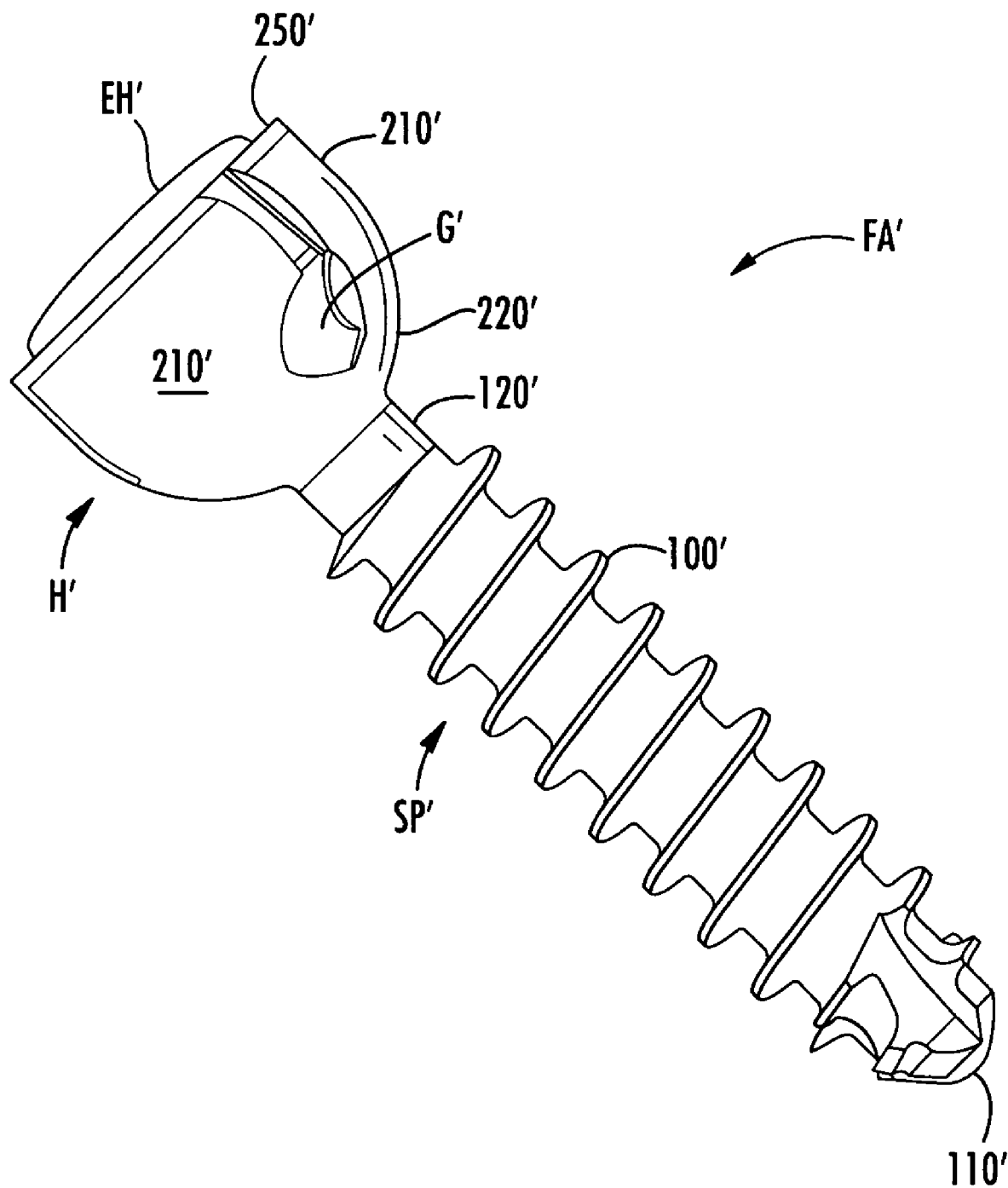
FIG. 16 of the drawings is a side view of the laterally-fixed fixation apparatus shown in FIG. 15.

Referring now to FIGS. 15 and 16, another embodiment of the present subject matter is shown. As known to those of skill in the art, bone fracture plates commonly used in orthopedics can comprise fixed-angle screw orientations or variable-angle screw orientations. Plates with fixed-angle screw orientations can provide maximum stability in bone conditions of poor quality and facilitate screw placement by having common screw orientations permanently fixed into the plate. However, disadvantages of these fixed-angle systems are known, such as the inability to allow for significant lagging or rotation of the screw after contact with the plate to compress the bone and plate together. Plates with variable-angle screw orientations are also used, which allow a surgeon a choice of screw placement to most optimally treat a patient's individual condition. However, disadvantages of these variable-angle systems are also known, such as the possibility of lateral movement of the plate and screw after implantation is complete.

While both types of prior art systems can be made with locking features to provide additional bending resistance at the interface of the plate and screw, or to prevent screw loosening or back-out, it is desirous to provide a system with the ability to lag plus the ability to restrict lateral toggling. As such, the fixation system of the present subject matter incorporates the advantages of fixation apparatus FA described above in a plate system allowing both fixed-angle (laterally-fixed) and variable-angle (laterally-variable) bone fastener orientation. More particularly with reference to FIG. 15, fixation system FS can include a device which can be a planar device, such as plate P described above, having one or more holes such as holes 400 and a planar surface 412 (which abuts a bone surface when installed). It is envisioned that plate P can be in any shape (round washer, etc.) and can be constructed of any biocompatible material such as titanium, titanium alloy, stainless steel, cobalt chromium, or any absorbable material such as PLLA or polycarbonate. Holes 400 can be generally spherical, conical, or rounded at base portion 406 closest to the bone surface and preferably has walls of a cylindrical shape (or other constant geometric shape).

Fixation system FS further can include at least one laterally-variable fixation apparatus FA, as described above with reference to FIGS. 1 and 2. Variable fixation apparatus FA can have a generally spherical, conical, or rounded shaped head portion H wherein variable fixation apparatus FA can rotate about a longitudinal axis as shown by arrow A3 and is also capable of toggling laterally relative to planar surface 412 of plate P, as shown by arrow A4. With reference to FIG. 16, fixation system FS further can include at least one laterally-fixed fixation apparatus FA'. Fixed fixation apparatus FA' can be generally comparable to variable fixation apparatus FA as described above, but can comprise wall sections 210' designed to provide a generally cylindrical shaped (or other constant geometric shape) head portion H'. Cylindrical shaped head portion H' of fixed fixation apparatus FA' can engage the cylindrical walls of hole 400 as shown in FIG. 15 so as to prevent angulation of fixed fixation apparatus FA' by engaging more contact surface of hole 400 in plate P. This design allows for rotation of fixed fixation apparatus FA' about a longitudinal axis as shown by arrow A3', but can restrict lateral toggle movement relative to planar surface 412 of plate P. Both variable fixation apparatus FA and fixed fixation apparatus FA' can include expander hub EH, EH' for locking of fixation apparatus FA, FA' to plate P, the operation of which is described in more detail above. More particularly, expander hub EH, EH' can be rotated using any suitable driver to force at least one or more of head wall sections 210, 210' outwardly against the walls of hole 400 until sufficient pressure is exerted by wall sections 210, 210' against the walls of hole 400 to maintain and lock fixation apparatus FA, FA' to plate P.

Either variable fixation apparatus FA or fixed fixation apparatus FA' can have additional locking features for locking of fixation apparatus FA, FA' to plate P. Such locking features can include a tab, ring, or protrusion formed on fixation apparatus FA, FA' that interlocks with a receiving section formed in hole 400 of plate P. Alternatively, fixation apparatus FA, FA' can have a receiving section that interlocks with a protruding section formed on plate P. As described above, since the heads of fixation apparatus FA, FA' may be thicker than desired (especially if additional features, such as locking, are included), it may be necessary to countersink into the bone to allow the fixation apparatus to sit in a thinner plate. As such, fixation apparatus FA, FA' may be self-counterboring such as though the addition of groove G (see FIGS. 2 and 16) that can be defined in the lower portion of head portion H, H'. Finally, holes 400 formed in plate P can be designed to allow either of variable fixation apparatus FA or fixed fixation apparatus FA' to be used therein. Alternatively, plate P can combine different types of holes 400 to make some specifically adaptable to receive variable fixation apparatuses FA and others specifically adaptable to receive fixed fixation apparatuses FA'.

Figure 17A:
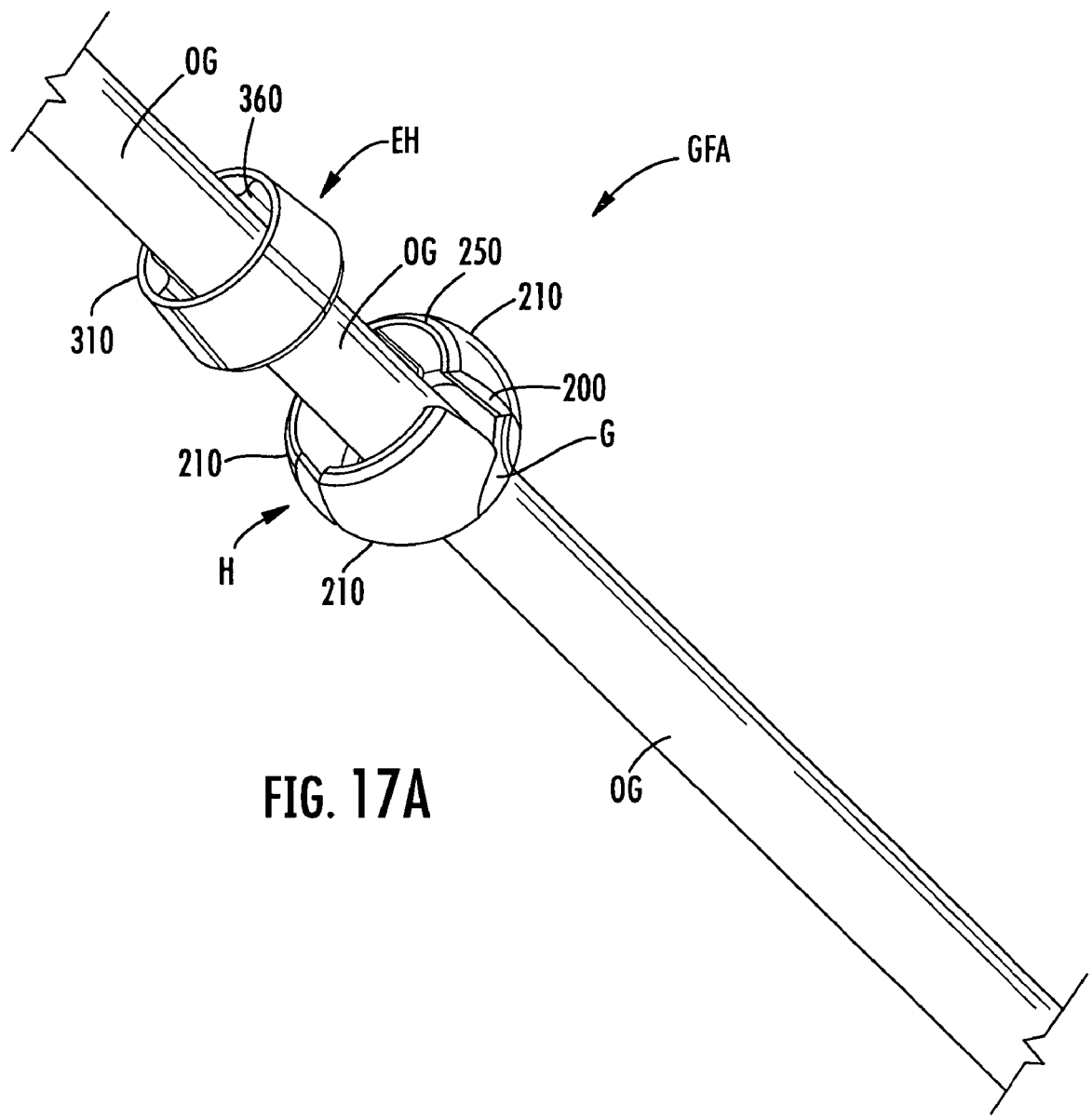
FIGS. 17A and 17B of the drawings are perspective views of an embodiment of a guide fixation apparatus with an expander hub shown detached.
Figure 17B:
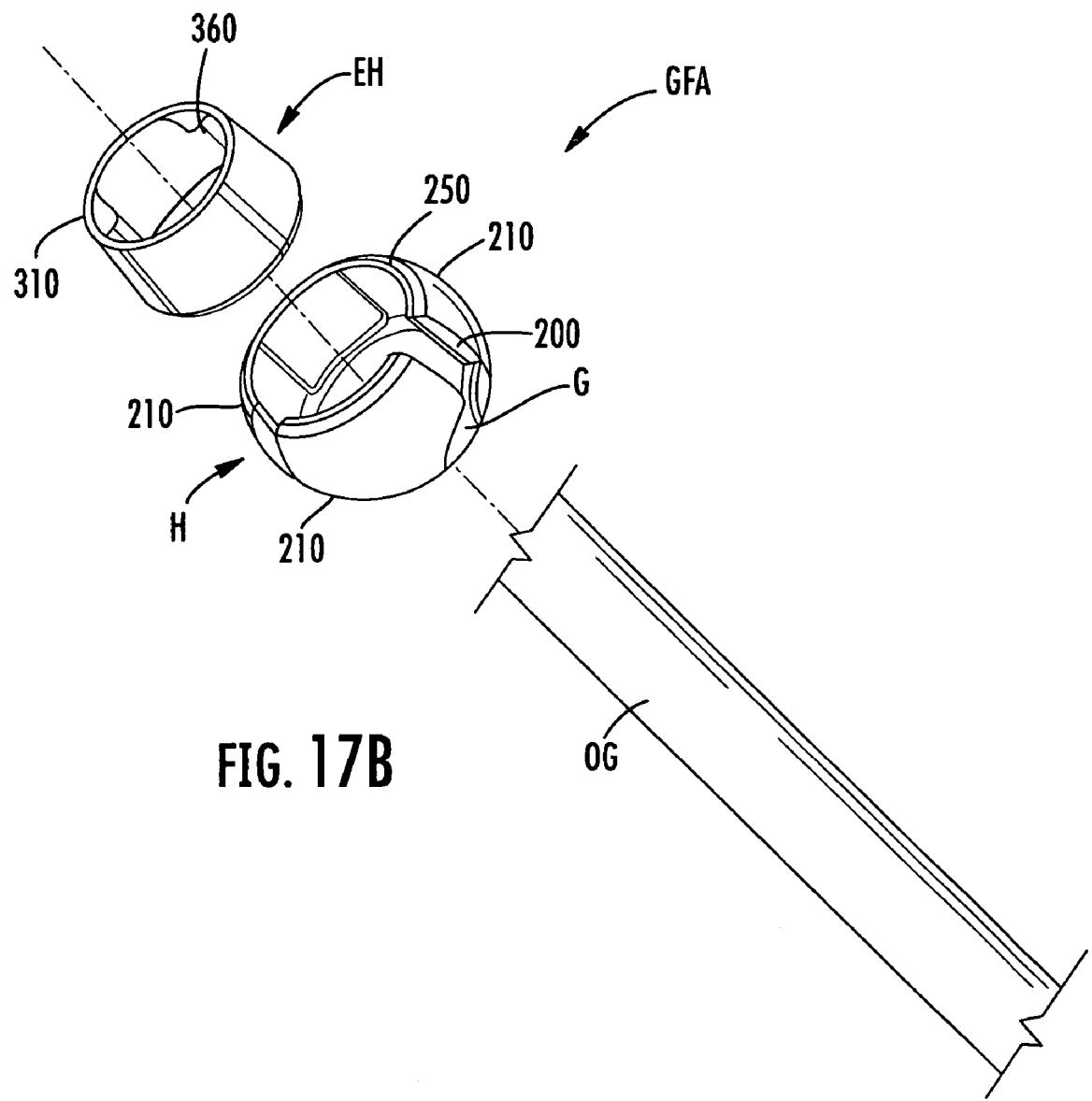
Figure 18:
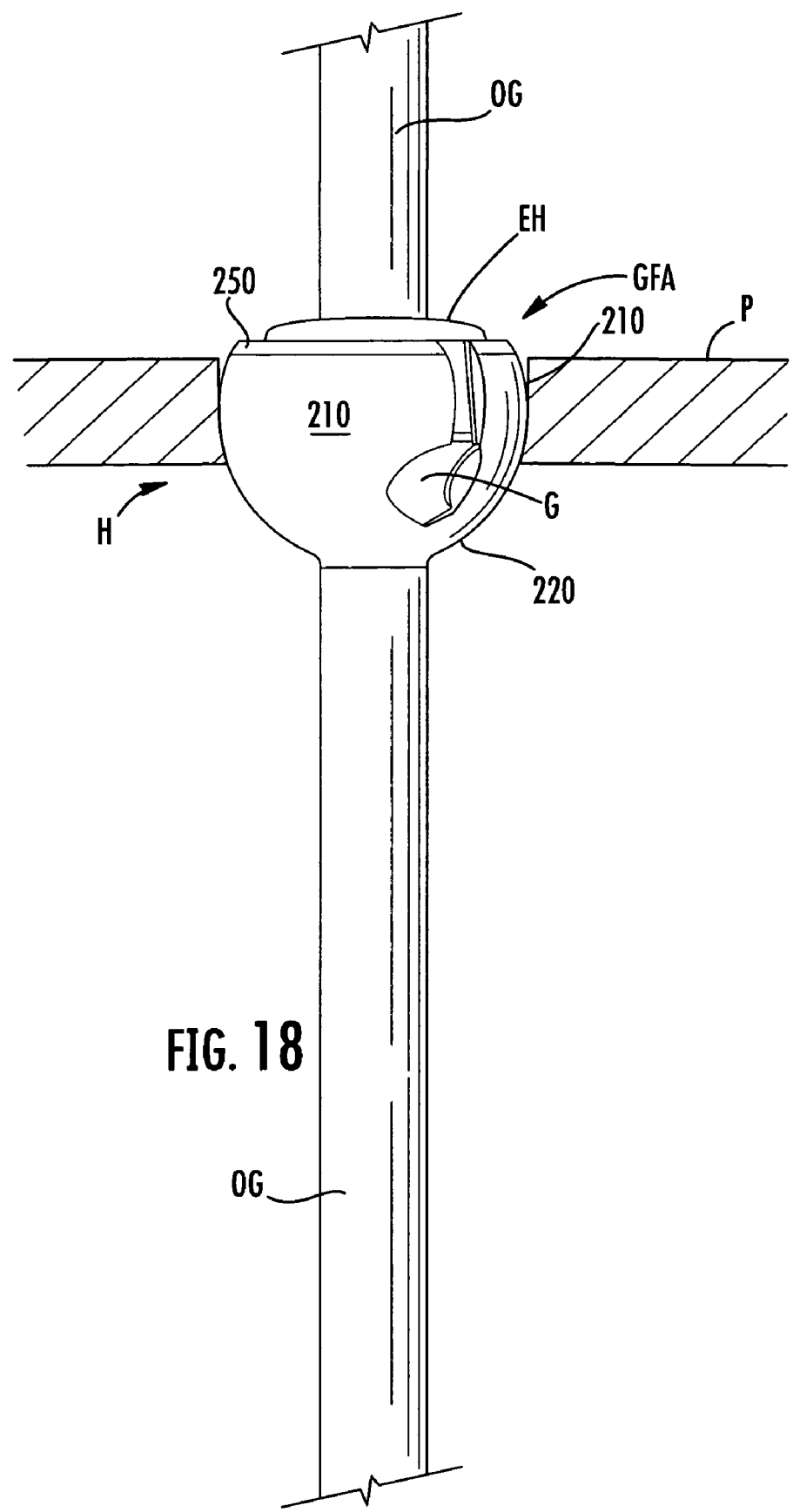
FIG. 18 of the drawings is a side view of the guide fixation apparatus shown in FIGS. 17A and 17B with the expander hub attached and engaged with a plate.

Referring now to FIGS. 17A, 17B and 18, a further embodiment of the present subject matter is shown. It is known in the art that sometimes bone fasteners, such as screws, may be too large or otherwise undesirable for fixating small fragments of bone. In these situations, surgeons may use a guide (threaded or non-threaded), such as a rod or a K wire, to stabilize the bone fragments. When such guides are used for such stabilization, it is known that the guides can sometimes migrate longitudinally which can result in protrusion of the guide into sensitive tissues or possibly destabilization of the bone fragments that are being held together. As such, it is desirable to have a system that can constrain orthopedic guides to a plate for fixating of bone fragments without the aforementioned undesirable effects of guide migration.

As illustrated in FIGS. 17A, 17B and 18, a guide fixation apparatus generally designated GFA is provided to fixate an orthopedic guide OG to a plate P. All components of guide fixation apparatus GFA can be separate and independent of one another. As shown, guide fixation apparatus GFA can include a head portion H and expander hub EH, both of which are substantially similar in design concept to those described in more detail above with reference to fixation apparatus FA (separate and independent from shank portion SP). More particularly, head portion H can have one or more slots, such as slots 200, defined through portions of the wall of head portion H to create wall sections 210. Additionally, expander hub EH can have slots or slits (not shown), or be made of a malleable material, such that wall sections 360 are moveable inwardly or outwardly when under pressure. Expander hub EH can be positioned within head portion H in a disengaged or unlocked position wherein wall sections 210 of head portion H are not forced outwardly, and an engaged or locked position wherein wall sections 210 of head portion H are forced outwardly sufficient to lock guide fixation apparatus GFA in a predetermined position within plate P. It is additionally envisioned that when expander hub EH is in the engaged or locked position, orthopedic guide OG can also be locked, such as by forcing inner wall sections 360 of expander hub EH inwardly, so as to prevent any longitudinal migration of guide OG within plate P. It is additionally understood that once guide fixation apparatus GFA has been engaged or locked such that guide OG is fixed laterally and longitudinally within plate P, the length of guide OG may be adjusted through the use of pre-stressed or pre-fatigued regions or notches (not shown) formed in guide OG wherein portions of guide OG can be broken off at certain lengths, such as for example a length generally flush with uppermost surface 310 of expansion hub EH.

Figure 19:
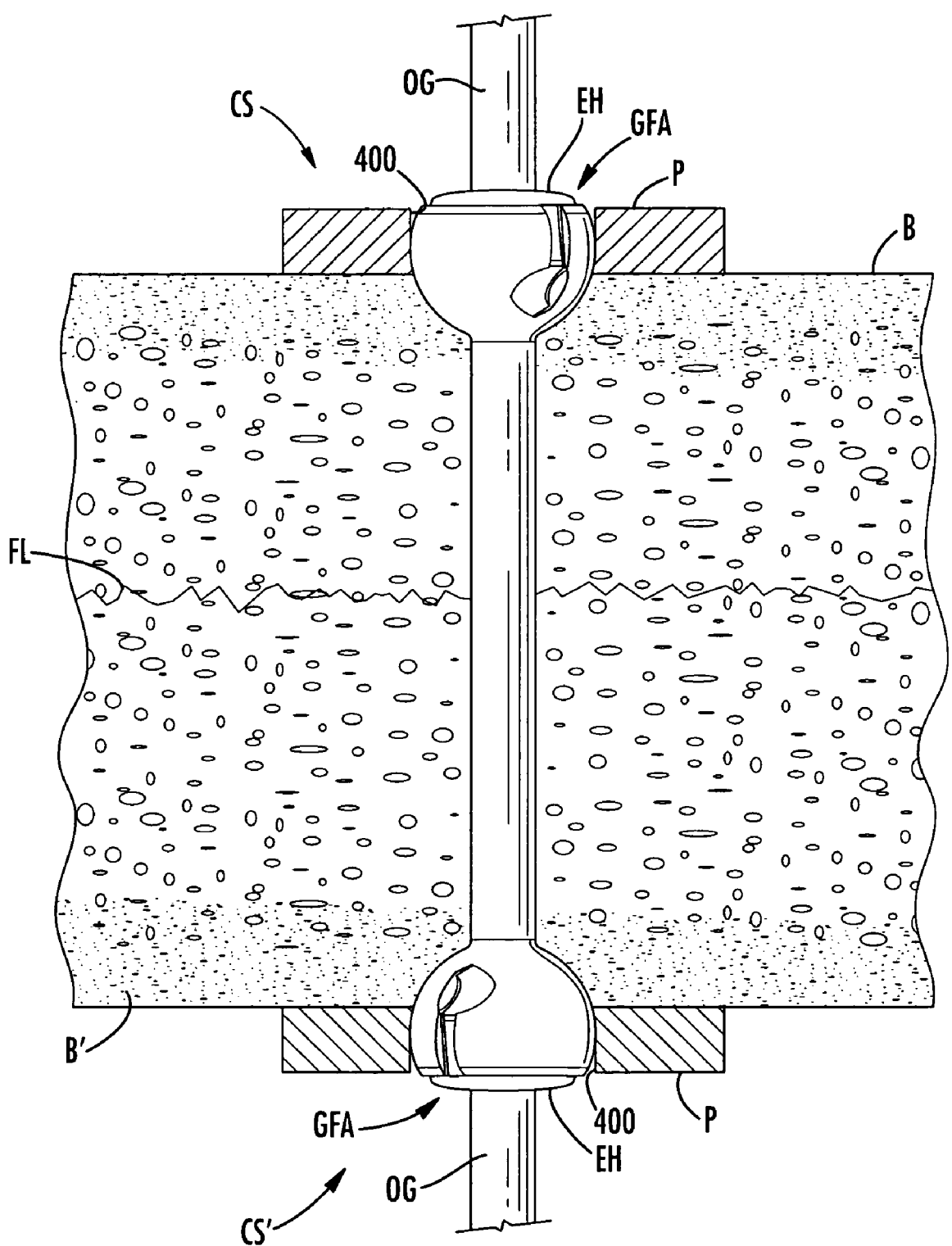
FIG. 19 of the drawings is a sectional view illustrating two guide fixation apparatuses and a guide locked in place against two plates to fixate a fractured bone.

Referring now to FIG. 19, systems and methods are provided for compressing two bone portions B, B', which are separated by a break or fracture line FL. The system can include an orthopedic guide OG and first and second compression fixation systems CS, CS'. Each compression system CS, CS' includes a plate P and a guide fixation apparatus GFA, the structure and function of which is described above. In operation, a surgeon can drive an orthopedic guide OG across first and second bone portions B, B' and fracture line FL. Plates P and guide fixation apparatuses GFA of first and second compression systems CS, CS' can be positioned against first and section bone portions B, B', respectively, and guide OG can be positioned within holes 400 of plates P and through openings defined within guide fixation apparatuses GFA of first and second compression systems CS, CS'. First and second compression systems CS, CS' and respective first and second bone portions B, B' can then be compressed together to form a unitary structure. After compression of first and second bone portions B, B' is complete, each guide fixation apparatus GFA can be rotated using a suitable driver into an engaged or locked position as described above wherein guide OG is locked laterally and longitudinally with respect to each plate P of first and second compression systems CS, CS', thereby holding first and second bone portions B, B' in compression. Once locking is complete, portions of guide OG can be removed, for example at predetermined notch points as described above.

It will be understood that various details of the subject matter disclosed herein may be changed without departing from the scope of the subject matter. Furthermore, the foregoing description is for the purpose of illustration only, and not for the purpose of limitation.

That which is claimed:

1. A fixation system for fixating bone, the fixation system comprising:
   (a) a planar fixation device having a planar surface and defining at least one opening therethrough, the opening having side walls defining an at least generally cylindrical shape; and
   (b) a laterally-fixed fixation apparatus comprising:
      (i) an at least generally cylindrical shaped head portion comprising plurality of outer wall sections at least partially surrounding a central hollow area with the outer wall sections having inner sides facing the central hollow area, the head portion having an inner bottom planar surface below the central hollow area and a top end with the inner sides of the outer wall sections tapered inwardly toward the central hollow area from the inner bottom surface to the top end;
      (ii) an expander hub adapted for positioning at least partially within the central hollow area and seated at least partially on the inner bottom planar surface of the cylindrical head portion, the expander hub being rotatable to force at least one or more of the outer wall sections of the head portion outwardly; and
      (iii) wherein the fixation apparatus is adapted to be positioned at least partially in the opening of the planar fixation device where the expander hub of the fixation apparatus is rotatable to force at least one or more of the outer wall sections of the head portion outwardly against a portion of the side walls of the opening to lock the fixation apparatus in a desired position in the opening and further wherein the fixation apparatus is adapted for rotation about a longitudinal axis of the fixation apparatus without lateral toggle movement relative to the planar surface of the planar fixation device while the fixation apparatus is positioned at least partially in the opening.

2. The fixation system according to claim 1 wherein the planar fixation device is a plate.

3. The fixation system according to claim 1 wherein the planar fixation device is a washer.

4. The fixation system according to claim 1 wherein the laterally-fixed fixation apparatus comprises a shank portion extending from the head portion.

5. The fixation system according to claim 4 wherein the shank portion is integral and formed as an extension of the head portion.

6. The fixation system according to claim 4 wherein the shank portion is separate from and extends from the head portion.

7. The fixation system according to claim 4 wherein the shank portion is threaded.

8. The fixation system according to claim 4 wherein the shank portion is non-threaded.

9. The fixation system according to claim 1 wherein the head portion of the laterally-fixed fixation apparatus is self-counterboring.

10. The fixation system according to claim 1 wherein the wall sections of the head portion of the fixation apparatus comprise a plurality of wall sections extending from a portion of the fixation apparatus, the wall sections defining slots between each wall section which provide a space between adjacent wall sections.

11. The fixation system according to claim 10 wherein the slots are at least substantially parallel to one another.

12. The fixation system according to claim 11 comprising a shank portion extending from the head portion and wherein the slots of the head portion extend in a direction at least substantially parallel to an axis along which the shank portion extends.

13. The fixation system according to claim 1 wherein the inner bottom surface of the head portion of the fixation apparatus defines a recessed opening.

14. The fixation system according to claim 1 wherein the inner bottom surface of the head portion of the fixation apparatus further comprises an at least partially inclined bottom surface.

15. The fixation system according to claim 14 wherein the expander hub has a bottom surface that is at least partially inclined.

16. The fixation system according to claim 1 wherein the expander hub of the fixation apparatus is at least generally cylindrical.

17. The fixation system according to claim 16 wherein the expander hub comprises an inclined bottom surface.

18. The fixation system according to claim 1 wherein the expander hub of the fixation apparatus comprises a plurality of lobes on an outer surface of the expander hub.

19. The fixation system according to claim 18 wherein the lobes on the expander hub extend outwardly.

20. The fixation system according to claim 1 wherein the expander hub of the fixation apparatus comprises a plurality of annular recesses for receiving a driver for rotating the expander hub.

21. A fixation system for fixating bone, the fixation system comprising:
   (a) a planar fixation device having a planar surface and defining a plurality of openings therethrough, the openings having side walls defining an at least generally cylindrical shape;
   (b) at least one laterally-variable fixation apparatus comprising:
      (i) an at least generally spherical shaped head portion comprising a plurality of outer wall sections at least partially surrounding a central hollow area, the head portion having an at least partially inclined inner bottom surface below the central hollow area;
      (ii) an expander hub having an at least partially inclined bottom surface, the expander hub adapted for positioning at least partially within the central hollow area and seated at least partially on the at least partially inclined inner bottom surface of the spherical head portion such that the at least partially inclined bottom surface of the expander hub and the at least partially inclined inner bottom surface of the spherical head portion rest in a fitted position with the at least partially inclined bottom surface of the expander hub substantially matching the at least partially inclined inner bottom surface of the spherical head portion, the expander hub being rotatable to cause the expander hub to rise in the central hollow area relative to the spherical head portion into a locked position to force at least one or more of the outer wall sections of the head portion outwardly; and
      (iii) wherein the laterally-variable fixation apparatus is adapted to be positioned at least partially in an opening of the planar fixation device where the expander hub of the laterally-variable fixation apparatus is rotatable to force at least one or more of the outer wall sections of the head portion outwardly against a portion of the side walls of the opening to lock the laterally-variable fixation apparatus in a desired position in the opening and further wherein the laterally-variable fixation apparatus is adapted for rotation about a longitudinal axis of the laterally-variable fixation apparatus and is adapted for lateral toggle movement relative to the planar surface of the planar fixation device while the laterally-variable fixation apparatus is positioned at least partially in the opening; and
(c) at least one laterally-fixed fixation apparatus comprising:
  (i) an at least generally cylindrical shaped head portion comprising a plurality of outer wall sections at least partially surrounding a central hollow area, the head portion having an at least partially inclined inner bottom surface below the central hollow area;
  (ii) an expander hub having an at least partially inclined bottom surface, the expander hub adapted for positioning at least partially within the central hollow area and seated at least partially on the at least partially inclined inner bottom surface of the cylindrical head portion such that the at least partially inclined bottom surface of the expander hub and the at least partially inclined inner bottom surface of the cylindrical head portion rest in a fitted position with the at least partially inclined bottom surface of the expander hub substantially matching the at least partially inclined inner bottom surface of the spherical head portion, the expander hub being rotatable to cause the expander hub to rise in the central hollow area relative to the cylindrical head portion into a locked position to force at least one or more of the outer wall sections of the head portion outwardly; and
  (iii) wherein the laterally-fixed fixation apparatus is adapted to be positioned at least partially in an opening of the planar fixation device where the expander hub of the laterally-fixed fixation apparatus is rotatable to force at least one or more of the outer wall sections of the head portion outwardly against a portion of the side walls of the opening to lock the laterally-fixed fixation apparatus in a desired position in the opening and further wherein the laterally-fixed fixation apparatus is adapted for rotation about a longitudinal axis of the laterally-fixed fixation apparatus without lateral toggle movement relative to the planar surface of the planar fixation device while the laterally-fixed fixation apparatus is positioned at least partially in the opening.

22. A fixation system for fixating an orthopedic guide, the fixation system comprising:
(a) a planar fixation device having a planar surface and defining at least one opening therethrough; and
(b) a guide fixation apparatus adapted for receiving an orthopedic guide, the fixation apparatus comprising:
  (i) a head portion comprising a plurality of outer wall sections at least partially surrounding a central hollow area, the head portion having an at least partially inclined inner bottom surface below the central hollow area;
  (ii) an expander hub having an at least partially inclined bottom surface, the expander hub adapted for positioning at least partially within the central hollow area and seated at least partially on the inner bottom surface of the head portion such that the at least partially inclined bottom surface of the expander hub and the at least partially inclined inner bottom surface of the head portion rest in a fitted position with the at least partially inclined bottom surface of the expander hub substantially matching the at least partially inclined inner bottom surface of the spherical head portion, the expander hub having side walls and a bottom surface having an opening defined therein adapted for receiving the orthopedic guide, and the expander hub being rotatable to cause the expander hub to rise in the central hollow area relative to the head portion into a locked position to force at least one or more of the outer wall sections of the head portion outwardly; and
  (iii) wherein the guide fixation apparatus is adapted to be positioned at least partially in the opening of the planar fixation device where the expander hub of the fixation apparatus is rotatable to force at least one or more of the outer wall sections of the head portion outwardly against a portion of the side walls of the opening to lock the fixation apparatus in a desired position in the opening.

23. The fixation system according to claim 22 wherein the planar fixation device is a plate.

24. The fixation system according to claim 22 wherein the planar fixation device is a washer.

25. The fixation system according to claim 22 wherein the wall sections of the head portion of the guide fixation apparatus comprise a plurality of wall sections extending from a portion of the guide fixation apparatus, the wall sections defining slots between each wall section which provide a space between adjacent wall sections.

26. The fixation system according to claim 25 wherein the slots are at least substantially parallel to one another.

27. The fixation system according to claim 22 wherein the expander hub of the guide fixation apparatus is at least generally cylindrical.

28. The fixation system according to claim 22 wherein the expander hub of the guide fixation apparatus comprises a plurality of lobes on an outer surface of the expander hub.

29. The fixation system according to claim 28 wherein the lobes on the expander hub extend outwardly.

30. The fixation system according to claim 22 wherein the expander hub of the guide fixation apparatus comprises a plurality of annular recesses for receiving a driver for rotating the expander hub.

31. The fixation system according to claim 22 wherein the side walls of the expander hub are moveable inwardly to lock an orthopedic guide in a desired position within the expander hub opening.

32. The fixation system according to claim 22 wherein the at least partially inclined bottom surface of the expander hub rotates against the inclined inner bottom surface of the spherical head portion to cause the expander hub to rise in the central hollow area relative to the cylindrical head portion into a locked position.

33. A system for compressing bone portions, the system comprising:
(a) an elongated orthopedic guide having first and second ends;
(b) first and second compression fixation systems, each fixation system comprising:
  (i) a planar fixation device having a planar surface and defining at least one opening therethrough, the planar fixation device adapted to be positioned against a bone portion; and
  (ii) a guide fixation apparatus adapted for receiving an orthopedic guide, the fixation apparatus comprising:
    1) a head portion comprising a plurality of outer wall sections at least partially surrounding a central hollow area, the head portion having an inner bottom surface below the central hollow area;
    2) an expander hub adapted for positioning at least partially within the central hollow area and seated at least partially on the inner bottom surface of the head portion, the expander hub having side walls and a bottom surface having an opening defined therein adapted for receiving the orthopedic guide, and the expander hub being rotatable to force at least one or more of the outer wall sections of the head portion outwardly; and 3) wherein the guide fixation apparatus is adapted to be positioned at least partially in the opening of the planar fixation device where the expander hub of the fixation apparatus can be rotated to force at least one or more of the outer wall sections of the head portion outwardly against a portion of the side walls of the opening to lock the fixation apparatus in a desired position in the opening; and (c) wherein the planar fixation device and guide fixation apparatus of the first compression fixation system receive the first end of the orthopedic guide and the planar fixation device and guide fixation apparatus of the second compression fixation system receive the second end of the orthopedic guide when the elongated orthopedic guide, the first compression fixation system and the second compression fixation system are assembled to compress bone.

34. The system according to claim 33 wherein the planar fixation device of each of the first and second fixation systems is a plate.

35. The system according to claim 33 wherein the planar fixation device of each of the first and second fixation systems is a washer.

36. The system according to claim 33 wherein the side walls of the expander hub of each of the first and second fixation systems are moveable inwardly to lock the orthopedic guide in a desired position within the expander hub opening of each respective fixation system.

37. The system according to claim 33 wherein the head portion of each fixation apparatus has a top end and the outer wall sections of the head portion have inner sides facing the central hollow area with the inner sides of the outer wall sections tapered inwardly toward the central hollow area from the inner bottom surface to the top end.

38. The fixation system according to claim 37 wherein the at least partially inclined bottom surface of the expander hub rotates against the inclined inner bottom surface of the spherical head portion to cause the expander hub to rise in the central hollow area relative to the cylindrical head portion into a locked position.

39. The system according to claim 33 wherein the head portion of each fixation apparatus has an at least partially inclined inner bottom surface below the central hollow area and the expander hub has an at least partially inclined bottom surface such that when seated the at least partially inclined bottom surface of the expander hub rests in a fitted position on the at least partially inclined inner bottom surface of the cylindrical head portion with the expander hub being rotatable to cause the expander hub to rise in the central hollow area relative to the cylindrical head portion into a locked position to force at least one or more of the outer wall sections of the head portion outwardly.

40. A method of compressing bone portions, the method comprising:

(a) providing first and second compression fixation systems, each fixation system comprising:

(i) a planar fixation device having a planar surface and defining at least one opening therethrough; and (ii) a guide fixation apparatus for receiving an orthopedic guide, the fixation apparatus comprising:

1) a head portion comprising a plurality of outer wall sections at least partially surrounding a central hollow area, the head portion having an inner bottom surface below the central hollow area, the inner bottom having an opening defined therein for receiving the orthopedic guide;

2) an expander hub adapted for positioning at least partially within the central hollow area and seated at least partially on the inner bottom surface of the head portion, the expander hub having a bottom surface having an opening defined therein for receiving the orthopedic guide, and the expander hub being rotatable to force at least one or more of the outer wall sections of the head portion outwardly; and 3) wherein the guide fixation apparatus is adapted to be positioned at least partially in the opening of the planar fixation device where the expander hub of the fixation apparatus can be rotated to force at least one or more of the outer wall sections of the head portion outwardly against a portion of the side walls of the opening to lock the fixation apparatus in a desired position in the opening;

(b) driving an orthopedic guide into first and second bone portions;

(c) positioning the planar fixation device and guide fixation apparatus of the first fixation system against the first bone portion and positioning the planar fixation device and guide fixation apparatus of the second fixation system against the second bone portion;

(d) positioning the orthopedic guide in a desired alignment with respect to the planar fixation devices of the first and second fixation systems;

(e) compressing the first and second fixation systems wherein their respective first and second bone portions are compressed together; and (f) after compressing the bone, locking the guide fixation apparatus in position relative to the planar fixation device for each of the first and second fixation systems.

41. The method of claim 40 wherein the step of locking the guide fixation apparatus in position relative to the planar fixation device for each of the first and second fixation systems comprises rotating each respective expander hub to force at least one wall section of each respective head portion of each respective fixation apparatus outwardly.

42. A fixation system for fixating bone, the fixation system comprising:

(a) a planar fixation device having a planar surface and defining at least one opening therethrough, the opening having side walls defining an at least generally cylindrical shape; and (b) a laterally-fixed fixation apparatus comprising:

(i) an at least generally cylindrical shaped head portion comprising plurality of outer wall sections at least partially surrounding a central hollow area, the head portion having an at least partially inclined inner bottom surface below the central hollow area;

(ii) an expander hub having an at least partially inclined bottom surface, the expander hub adapted for positioning at least partially within the central hollow area and seated at least partially on the at least partially inclined inner bottom surface of the cylindrical head portion such that the at least partially inclined bottom surface of the expander hub and the at least partially inclined inner bottom surface of the cylindrical head portion rest in a fitted position with the at least partially inclined bottom surface of the expander hub substantially matching the at least partially inclined inner bottom surface of the spherical head portion, the expander hub being rotatable to cause the expander hub to rise in the central hollow area relative to the cylindrical head portion into a locked position to force at least one or more of the outer wall sections of the head portion outwardly; and (iii) wherein the fixation apparatus is adapted to be positioned at least partially in the opening of the planar fixation device where the expander hub of the fixation apparatus is rotatable to force at least one or more of the outer wall sections of the head portion outwardly against a portion of the side walls of the opening to lock the fixation apparatus in a desired position in the opening and further wherein the fixation apparatus is adapted for rotation about a longitudinal axis of the fixation apparatus without lateral toggle movement relative to the planar surface of the planar fixation device while the fixation apparatus is positioned at least partially in the opening.

43. A fixation system for fixating bone, the fixation system comprising:

(a) a planar fixation device having a planar surface and defining a plurality of openings therethrough, the openings having side walls defining an at least generally cylindrical shape;

(b) at least one laterally-variable fixation apparatus comprising:

(i) an at least generally spherical shaped head portion comprising a plurality of outer wall sections at least partially surrounding a central hollow area with the outer wall sections having inner sides facing the central hollow area, the head portion having an inner bottom planar surface below the central hollow area and a top end with the inner sides of the outer wall sections tapered inwardly toward the central hollow area from the inner bottom surface to the top end;

(ii) an expander hub adapted for positioning at least partially within the central hollow area and seated at least partially on the inner bottom planar surface of the spherical head portion, the expander hub being rotatable to force at least one or more of the outer wall sections of the head portion outwardly; and (iii) wherein the laterally-variable fixation apparatus is adapted to be positioned at least partially in an opening of the planar fixation device where the expander hub of the laterally-variable fixation apparatus is rotatable to force at least one or more of the outer wall sections of the head portion outwardly against a portion of the side walls of the opening to lock the laterally-variable fixation apparatus in a desired position in the opening and further wherein the laterally-variable fixation apparatus is adapted for rotation about a longitudinal axis of the laterally-variable fixation apparatus and is adapted for lateral toggle movement relative to the planar surface of the planar fixation device while the laterally-variable fixation apparatus is positioned at least partially in the opening; and (c) at least one laterally-fixed fixation apparatus comprising:

(i) an at least generally cylindrical shaped head portion comprising a plurality of outer wall sections at least partially surrounding a central hollow area with the outer wall sections having inner sides facing the central hollow area, the head portion having an inner bottom planar surface below the central hollow area and a top end with the inner sides of the outer wall sections tapered inwardly toward the central hollow area from the inner bottom surface to the top end;

(ii) an expander hub adapted for positioning at least partially within the central hollow area and seated at least partially on the inner bottom planar surface of the cylindrical head portion, the expander hub being rotatable to force at least one or more of the outer wall sections of the head portion outwardly; and (iii) wherein the laterally-fixed fixation apparatus is adapted to be positioned at least partially in an opening of the planar fixation device where the expander hub of the laterally-fixed fixation apparatus is rotatable to force at least one or more of the outer wall sections of the head portion outwardly against a portion of the side walls of the opening to lock the laterally-fixed fixation apparatus in a desired position in the opening and further wherein the laterally-fixed fixation apparatus is adapted for rotation about a longitudinal axis of the laterally-fixed fixation apparatus without lateral toggle movement relative to the planar surface of the planar fixation device while the laterally-fixed fixation apparatus is positioned at least partially in the opening.

44. A fixation system for fixating an orthopedic guide, the fixation system comprising:

(a) a planar fixation device having a planar surface and defining at least one opening therethrough; and (b) a guide fixation apparatus adapted for receiving an orthopedic guide, the fixation apparatus comprising:

(i) a head portion comprising a plurality of outer wall sections at least partially surrounding a central hollow area with the outer wall sections having inner sides facing the central hollow area, the head portion having an inner bottom planar surface below the central hollow area and a top end with the inner sides of the outer wall sections tapered inwardly toward the central hollow area from the inner bottom surface to the top end;

(ii) an expander hub adapted for positioning at least partially within the central hollow area and seated at least partially on the inner bottom planar surface of the head portion, the expander hub having side walls and a bottom surface having an opening defined therein adapted for receiving the orthopedic guide, and the expander hub being rotatable to force at least one or more of the outer wall sections of the head portion outwardly; and (iii) wherein the guide fixation apparatus is adapted to be positioned at least partially in the opening of the planar fixation device where the expander hub of the fixation apparatus is rotatable to force at least one or more of the outer wall sections of the head portion outwardly against a portion of the side walls of the opening to lock the fixation apparatus in a desired position in the opening.

* * * * *

UNITED STATES PATENT AND TRADEMARK OFFICE
CERTIFICATE OF CORRECTION

| | |
|---|---|
| PATENT NO. | : 7,691,133 B2 |
| APPLICATION NO. | : 11/292333 |
| DATED | : April 6, 2010 |
| INVENTOR(S) | : Partin et al. |

Page 1 of 1

It is certified that error appears in the above-identified patent and that said Letters Patent is hereby corrected as shown below:

On the title page, item 63 – Please insert:

--(63) Related U.S. Application Data

Continuation-in-part of application No. 11/010,825, filed on December 13, 2004--

Signed and Sealed this

Eighth Day of June, 2010

David J. Kappos
*Director of the United States Patent and Trademark Office*